United States Patent
Divita et al.

(10) Patent No.: US 9,598,465 B2
(45) Date of Patent: Mar. 21, 2017

(54) CELL PENETRATING PEPTIDES FOR INTRACELLULAR DELIVERY OF MOLECULES

(71) Applicant: Centre National de la Recherche Scientifique, Paris (FR)

(72) Inventors: Gilles Divita, Mauguio (FR); Sebastien Deshayes, Montpellier (FR); Karidia Konate, Montpellier (FR); May Catherine Morris, Mauguio (FR)

(73) Assignee: AADIGEN LLC, Pacific Palisades, CA (US)

( * ) Notice: Subject to any disclaimer, the term of this patent is extended or adjusted under 35 U.S.C. 154(b) by 0 days.

(21) Appl. No.: 14/433,573

(22) PCT Filed: Oct. 4, 2013

(86) PCT No.: PCT/EP2013/070680
§ 371 (c)(1),
(2) Date: Apr. 3, 2015

(87) PCT Pub. No.: WO2014/053624
PCT Pub. Date: Apr. 10, 2014

(65) Prior Publication Data
US 2016/0060296 A1 Mar. 3, 2016

(30) Foreign Application Priority Data
Oct. 4, 2012 (WO) .................. PCT/IB2012/055344

(51) Int. Cl.
| | | |
|---|---|---|
| A61K 47/42 | (2006.01) | |
| A61K 47/48 | (2006.01) | |
| C07K 7/08 | (2006.01) | |
| C07K 14/00 | (2006.01) | |
| A61K 9/51 | (2006.01) | |
| A61K 38/00 | (2006.01) | |

(52) U.S. Cl.
CPC .................. *C07K 7/08* (2013.01); *A61K 9/51* (2013.01); *A61K 47/42* (2013.01); *A61K 47/48246* (2013.01); *A61K 47/48315* (2013.01); *A61K 47/48323* (2013.01); *C07K 14/001* (2013.01); *A61K 38/00* (2013.01)

(58) Field of Classification Search
CPC .. A61K 38/10; A61K 47/42; A61K 47/48246; A61K 47/48315; A61K 47/48323; C07K 7/08
See application file for complete search history.

(56) References Cited

U.S. PATENT DOCUMENTS

| | | |
|---|---|---|
| 7,514,530 B2 | 4/2009 | Divita et al. |
| 9,376,468 B2 | 6/2016 | Divita et al. |
| 2014/0227344 A1 | 8/2014 | Divita et al. |
| 2016/0089447 A1 | 3/2016 | Divita et al. |
| 2016/0115199 A1 | 4/2016 | Divita et al. |
| 2016/0145299 A1 | 5/2016 | Divita et al. |

FOREIGN PATENT DOCUMENTS

| | | |
|---|---|---|
| EP | 1 795 539 A1 | 6/2007 |
| WO | 2007/069090 A2 | 6/2007 |

OTHER PUBLICATIONS

International Search Report issued in corresponding International Patent Application No. PCT/EP2013/070680 dated Dec. 10, 2013.
Kurzawa et al., "PEP and CADY-mediated delivery of fluorescent peptides and proteins into living cells," *Biochimica et Biophysica Acta*, 1798: 2274-2285 (2010).
Barre-Sinoussi, F. et al. (May 20, 1983) "Isolation of a T-lymphotropic retrovirus from a patient at risk for acquired immune deficiency syndrome (AIDS)," *Science* 220(4599):868-71.
Crombez, L. et al. (e-pub. May 29, 2009). "Targeting cyclin B1 through peptide-based delivery of siRNA prevents tumor growth," *Nucleic Acids Research* 37(14):4559-4569.
Crombez, L. et al. (Jan. 2009, e-pub. Oct. 28, 2008). "A New Potent Secondary Amphipathic Cell-Penetrating Peptide for siRNA Delivery Into Mammalian Cells," *Mol. Ther.* 17(1):95-103.
Deshayes, S. et al. (2005). "Cell-penetrating Peptides: Tools for Intracellular Delivery of Therapeutics," *Cell Mol Life Sci.* 62:1839-1849.
Deshayes, S. et al. (2008, e-pub. Oct. 25, 2007). "Delivery of Proteins and Nucleic Acids Using a Non-Covalent Peptide-Based Strategy," *Adv. Drug Deliv. Rev.* 60:537-547.
Glover, D.J. et al. (Apr. 2005, e-pub. Mar. 10, 2005). "Towards Safe, Non-Viral Therapeutic Gene Expression in Humans," *Nat. Rev. Genet.* 6:299-310.
Heitz, F. et al. (2009, e-pub. Mar. 20, 2009). "Themed Section: Vector Design and Drug Delivery Review. Twenty Years of Cell-Penetrating Peptides: From Molecular Mechanisms to Therapeutics," *British Journal of Pharmacology* 157:195-206.
Mery, J. et al. (Jul./Aug. 1992). "Disulfide Bond as Peptide-Resin Linkage in Boc-Bzl SPPS, for Potential Biochemical Applications," *Pept Res.* 5(4):233-40.
Morris, M.C. et al. (1997). "A New Peptide Vector for Efficient Delivery of Oligonucleotides Into Mammalian Cells," *Nucleic Acids Res.* 25(14):2730-2736.
Morris, M.C. et al. (Dec. 2001). "A Peptide Carrier for the Delivery of Biologically Active Proteins Into Mammalian Cells," *Nat. Biotechnol.* 19:1173-1176.
Morris et al. (2007) "A non-covalent peptide-based carrier for in vivo delivery of DNA mimics," *Nucleic Acids Research* 35(7):e49, 10 pages.
Roisin, A. et al. (Mar. 5, 2004, e-pub. Dec. 10, 2003) "Inhibition of HIV-1 replication by cell-penetrating peptides binding Rev." *J. Biol. Chem.* 279(10):9208-14.
Verdine, G.L. et al. (2012). "Stapled peptides for Intracellular Drug Targets," Chapter 1 in Methods in Enzymology, 503:3-33.
Whitehead, K.A. et al. (Feb. 2009). "Knocking Down Barriers: Advances in siRNA Delivery," *Nat Rev Drug Discov.* 8:129-138.

*Primary Examiner* — Jeffrey E Russel
(74) *Attorney, Agent, or Firm* — Morrison & Foerster LLP

(57) ABSTRACT

A cell-penetrating peptide characterized in that it comprises an amino acid sequence: $X_1X_2X_3WWX_4X_5WAX_6X_3X_7X_8X_9X_{10}X_{11}X_{12}WX_{13}R$ (SEQ ID No: 10), wherein $X_1$, is beta-A or S, $X_2$ is L or none, $X_3$ is R or none, $X_4$ is L, R or G, $X_5$ is R, W or S, $X_6$ is S, P or T, $X_7$ is W or P, X8 is F, A or R, $X_9$ is S, L, P or R, $X_{10}$ is R or S, $X_{11}$ n is W or none, $X_{12}$ is A, R or none and $X_{13}$ is W or F, and wherein if $X_3$ is none, then $X_3$, $X_{11}$ and $X_{12}$ are none as well.

23 Claims, 16 Drawing Sheets

VEPEP9a1: (βA/S) LRWWLRWASRWFSRWAWWR HHHHHHHHHHH   SEQ ID NO: 1
VEPEP9a2: (βA/S) LRWWLRWASRWAWFR HHHHHHHHHHHH   SEQ ID NO: 2
VEPEP9b1: (βA/S) RWWLRWASRWALSWRWWR HHHHHHHHHHH   SEQ ID NO: 3
VEPEP9b2: (βA/S) RWWLRWASRWFLSWRWWR HHHHHHHHHHH   SEQ ID NO: 4
VEPEP9c1: (βA/S) RWWLRWAPRWFPSWRWWR HHHHH TTHH   SEQ ID NO: 5
VEPEP9c2: (βA/S) RWWLRWASRWAPSWRWWR HHHHHHHHHH   SEQ ID NO: 6
VEPEP9d: (βA/S) WWRWWASWARSWWR HHHHHHHHHHH   SEQ ID NO: 7
VEPEP9e: (βA/S) WWGSWATPRRRWWR HHHHHTT   SEQ ID NO: 8
VEPEP9f: (βA/S) WWRWWAPWARSWWR HHHHH THH   SEQ ID NO: 9

CELL PENETRATING PEPTIDES FOR INTRACELLULAR DELIVERY OF MOLECULES

This application is the National Stage filing of PCT/EP2013/070680, entitled "CELL PENETRATING PEPTIDES FOR INTRACELLULAR DELIVERY OF MOLECULES" with the International Filing Date of Oct. 4, 2013, which claims the benefit of priority from PCT/IB2012/055344, filed on Oct. 4, 2012.

The content of the following submission on ASCII text file is incorporated herein by reference in its entirety: a computer readable form (CRF) of the Sequence Listing (file name: VMAahF644s356_ST25 subsl.txt, date recorded: Jun. 23, 2016, size: 27 KB).

The present invention pertains to the field of intracellular delivery of molecules such as nucleic acids and small hydrophobic molecules. In particular, the invention relates to a new cell-penetrating peptide (CPP) family, which exhibits high efficacy, low toxicity and is particularly efficient for transdermal applications.

Although small molecules remain the major drugs used in clinic, in numerous cases, their therapeutic impact has reached limitations such as insufficient capability to reach targets, lack of specificity, requirement for high doses leading to toxicity and major side effects. Over the past ten years, in order to circumvent limitations of small molecules and of gene-based therapies, we have witnessed a dramatic acceleration in the discovery of larger therapeutic molecules such as proteins, peptides and nucleic acids which present a high specificity for their target but do not follow Lipinski's rules. Pharmaceutical potency of these molecules remains restricted by their poor stability in vivo and by their low uptake in cells. Therefore, "delivery" has become a central piece of the therapeutic puzzle and new milestones have been established to validate delivery strategies: (a) lack of toxicity, (b) efficiency at low doses in vivo, (c) easy to handle for therapeutic applications (d) rapid endosomal release and (e) ability to reach the target. Although viral delivery strategies had given much hope for gene and cellular therapies. their clinical application has suffered from side- and toxicity-effects [1,2]. Researches were mainly focused on the development of non-viral strategies, and different methods have been proposed including lipid, polycationic nanoparticles and peptide-based formulations, but only few of these technologies have been efficient in vivo and have reached the clinic. Cell Penetrating Peptides (CPP) are one of the most promising non-viral strategies. Although definition of CPPs is constantly evolving, they are generally described as short peptides of less than 30 amino acids either derived from proteins or from chimeric sequences. They are usually amphipathic and possess a net positive charge [3-5]. CPPs are able to penetrate biological membranes, to trigger the movement of various biomolecules across cell membranes into the cytoplasm and to improve their intracellular routing, thereby facilitating interactions with the target. CPPs can be subdivided into two main classes, the first requiring chemical linkage with the cargo and the second involving the formation of stable, non-covalent complexes. CPPs from both strategies have been reported to favour the delivery of a large panel of cargos (plasmid DNA, oligonucleotide, siRNA, PNA, protein, peptide, liposome, nanoparticle . . . ) into a wide variety of cell types and in vivo models [3-7].

Twenty years ago, the concept of protein transduction domain (PTD) was proposed based on the observation that some proteins, mainly transcription factors, could shuttle within cells and from one cell to another [for review see ref 3,4]. The first observation was made in 1988, by Frankel and Pabo. They showed that the transcription-transactivating (Tat) protein of HIV-1 could enter cells and translocate into the nucleus. In 1991, the group of Prochiantz reached the same conclusions with the *Drosophila* Antennapedia homeodoinain and demonstrated that this domain was internalized by neuronal cells. These works were at the origin of the discovery in 1994 of the first Protein Transduction Domain: a 16 mer-peptide derived from the third helix of the homeodomain of Antennapedia named Penetratin. In 1997, the group of Lebleu identified the minimal sequence of Tat required for cellular uptake and the first proofs-of-concept of the application of PTD in vivo, were reported by the group of Dowdy, for the delivery of small peptides and large proteins. Historically, the notion of Cell Penetrating Peptide (CPP) was introduced by the group of Langel, in 1998, with the design of the first chimeric peptide carrier, the Transportan, which derived from the N-terminal fragment of the neuropeptide galanin, linked to mastoparan, a wasp venom peptide. Transportan has been originally reported to improve the delivery of PNAs both in cultured cells and in vivo. In 1997, the group of Heitz and Divita proposed a new strategy involving CPP in the formation of stable but non-covalent complexes with their cargo [7]. The strategy was first based on the short peptide carrier (MPG) consisting of two domains: a hydrophilic (polar) domain and a hydrophobic (apolar) domain, MPG was designed for the delivery of nucleic acids [7]. The primary amphipathic peptide Pep-1 was then proposed for non-covalent delivery of proteins and peptides [8]. Then the groups of Wender and of Futaki demonstrated that polyarginine sequences (Arg8) are sufficient to drive small and large molecules into cells and in vivo. Ever since, many CPPs derived from natural or unnatural sequences have been identified and the list is constantly increasing. Peptides have been derived from VP22 protein of Herpes Simplex Virus, from calcitonin, from antimicrobial or toxin peptides, from proteins involved in cell cycle regulation, as well as from polyproline-rich peptides [reviews 4-6].

BRIEF DESCRIPTION OF THE DRAWINGS

FIG. 1 shows secondary structure prediction for various VEPEP-9 peptides. H: helix; T: turn.

FIG. 14 shows reduction of tumor growth by intravenous administration of NANOPEP particles containing antisense PNA targeting Cyclin B1 in SKB3-HEK2 xenograft mice. NANO-9A/PNA 5: VEPEP-9a/PNA core (5 μg PNA), coated with VEPEP-9a; NANO-9A/PNA 10: VEPEP-9a/PNA core (10 μg PNA), coated with VEPEP-9a; NANO-9A-PEG/PNA: VEPEP-9a/PNA core, coated with PEG-VEPEP-9a; NANO-9c/PNA 5: VEPEP-9c/PNA core (5 μg PNA), coated with VEPEP-9c; NANO-9c/PNA 10: VEPEP-9c/PNA core (10 μg PNA), coated with VEPEP-9c; NANO-9c/a-PEG/PNA: VEPEP-9c/PNA core, coated with PEG-VEPEP-9a.

DETAILED DESCRIPTION

Figure 2:
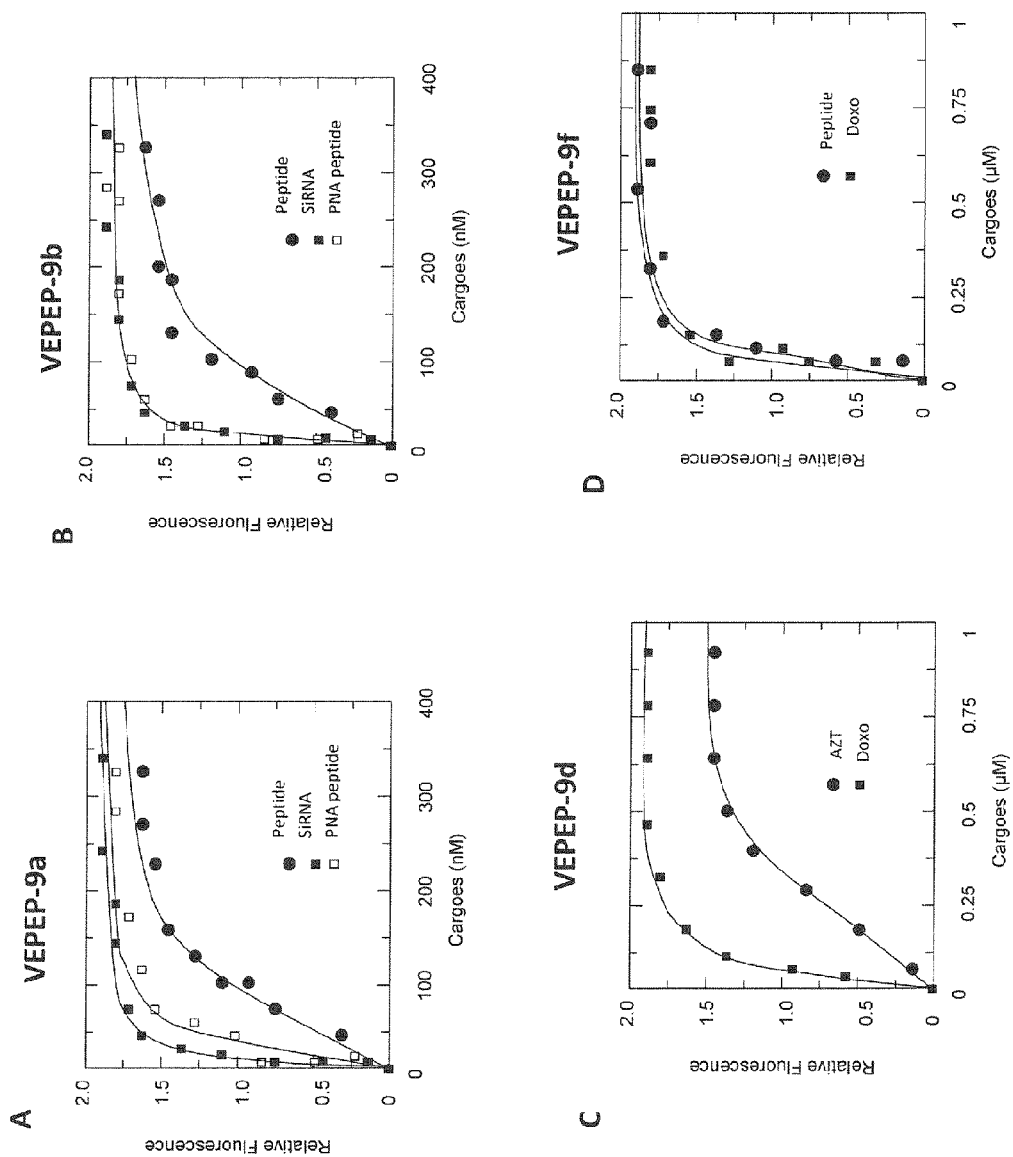
FIGS. 2A, 2B, 2C, and 2D show the binding of VEPEP-9a (2A), VEPEP-9b (2B), VEPEP-9d (2C), and VEPEP-9f (2D) peptides with various cargoes, as monitored by fluorescence spectroscopy using either intrinsic Trp of VEPEP-9 or extrinsic fluorescently labeled cargoes.

The inventors have now designed a new family of cell-penetrating peptides for the delivery of peptides/proteins, hydrophobic and charged molecules, named VEPEP-9. Delivery strategies using VEPEP-9 peptides as the outer layer of nanoparticles are referred to as NANOPEP-9.

VEPEP-9 are short secondary amphipathic peptides forming stable nanoparticles with molecules such as small peptides, peptide analogues, small oligonucleotides or derived and small hydrophobic or charged molecules, hereafter designated as "SHM". VEPEP-9 vectors comprise the following amino acid sequence: $X_1X_2X_3WWX_4X_5WAX_6X_3X_7X_8X_9X_{10}X_{11}X_{12}WX_{13}R$ (SEQ ID No: 10), wherein:

$X_1$ is beta-A or S;
$X_2$ is L or none;
$X_3$ is R or none;
$X_4$ is L, R or G;
$X_5$ is R, W or S;
$X_6$ is S, P or T;
$X_7$ is W or P;
$X_8$ is F, A or R;
$X_9$ is S, L, P or R;
$X_{10}$ is R or S;
$X_{11}$ is W or none;
$X_{12}$ is A, R or none; and
$X_{13}$ is W or F; and wherein if $X_3$ is none, then $X_2$, $X_{11}$ and $X_{12}$ are none as well.

According to a particular embodiment of the VEPEP-9 cell-penetrating peptides according to the invention, the vector comprises an amino acid sequence of 19 or 20 amino acids, which consists of: $X_1X_2RWWLRWAX_3RWX_4X_5X_6WX_7WX_8R$ (SEQ ID No: 11), wherein:

$X_1$ is beta-A or S;
$X_2$ is L or none;
$X_3$ is S or P;
$X_4$ is F or A;
$X_5$ is S, L or P;
$X_6$ is R or S;
$X_7$ is A or R; and
$X_8$ is W or F.

According to preferred embodiments of VEPEP-9 vectors as described in the above paragraph, illustrated in the experimental part below, the amino acid sequence of the cell-penetrating peptide is selected from the group consisting of

| | |
|---|---|
| VEPEP9a1:<br>$X_1$LRWWLRWASRWFSRWAWWR | (SEQ ID No: 1) |
| VEPEP9a2:<br>$X_1$LRWWLRWASRWASRWAWFR | (SEQ ID No: 2) |
| VEPEP9b1:<br>$X_1$RWWLRWASRWALSWRWWR, | (SEQ ID No: 3) |
| VEPEP9b2:<br>$X_1$RWWLRWASRWFLSWRWWR, | (SEQ ID No: 4) |
| VEPEP9c1:<br>$X_1$RWWLRWAPRWFPSWRWWR,<br>and | (SEQ ID No: 5) |
| VEPEP9c2:<br>$X_1$RWWLRWASRWAPSWRWWR, | (SEQ ID No: 6) | wherein $X_1$ is beta-A or S.

According to another embodiment of the VEPEP-9 cell-penetrating peptides according to the invention, the vector comprises an amino acid sequence of 15 amino acids, which consists of: $X_1WWX_2X_3WAX_4X_5X_6RX$ (SEQ ID No: 12), wherein:

X₁ is beta-A or S;
X₂ is R or G;
X₃ is W or S;
X₄ is S, T or P;
X₅ is W or P;
X₆ is A or R; and
X₇ is S or R.

According to preferred embodiments of VEPEP-9 vectors as described in the above paragraph, illustrated in the experimental part below, the amino acid sequence of the cell-penetrating peptide is selected from the group consisting of:

```
VEPEP9d:                    (SEQ ID No: 7)
X₁WWRWWASWARSWWR

VEPEP9e:                    (SEQ ID No: 8)
X₁WWGSWATPRRRWWR
and

VEPEP9f:                    (SEQ ID No 9)
X₁WWRWWAPWARSWWR,
``` wherein X₁ is beta-A or S.

According to a particular embodiment of the present invention, the VEPEP-9 cell penetrating peptide is stapled, which means that it comprises a chemical linkage (in addition to the amino acid chain) between two residues. In a particular embodiment of stapled VEPEP-9 peptides, the VEPEP-9 peptide comprises a hydrocarbon linkage between two residues which are separated by three or six residues. The skilled artisan can obtain these peptides by using techniques which are available in the art, for example as described by Verdine and Hilinski, Methods in Enzymology, 2012 [12].

VEPEP-9 strategy improves both ex-vivo and in vivo delivery and efficiency of peptide and analogue and small hydrophobic molecules, without activating the innate immune response or inducing toxic side effects.

According to a preferred embodiment, a cell-penetrating peptide of the present invention further comprises, covalently linked to the N-terminal end of the amino acid sequence, one or several chemical entities selected from the group consisting of an acetyl, a fatty acid, a cholesterol, a poly-ethylene glycol, a nuclear localization signal, a nuclear export signal, an antibody, a polysaccharide and a targeting molecule (peptide, fatty acid, saccharide).

As developed below and shown at least in example 5 below, PEGylation of VEPEP-9 peptides is particularly advantageous for stabilizing nanoparticles in vivo.

In addition or alternatively, a cell-penetrating peptide according to the invention can comprise, covalently linked to the C-terminal end of its amino acid sequence, one or several groups selected from the group consisting of a cysteamide, a cysteine, a thiol, an amide, a nitrilotriacetic acid optionally substituted, a carboxyl, a linear or ramified C1-C6 alkyl optionally substituted, a primary or secondary amine, an osidic derivative, a lipid, a phospholipid, a fatty acid, a cholesterol, a poly-ethylene glycol, a nuclear localization signal, nuclear export signal, an antibody, a polysaccharide and a targeting molecule.

Another aspect of the present invention is a complex comprising a cell-penetrating peptide as described above and a cargo selected amongst nucleic acids, proteins, peptides and hydrophobic molecules. Examples of polypeptide cargoes are small peptides, cyclic peptides, peptide-based biomarkers and bio-drugs. Examples of nucleic acid cargoes are charged or uncharged small oligonucleotides, such as, for example, small single stranded RNA or DNA (size between 2 to 40 bases) and double stranded RNA or DNA (size up to 100 base pairs), in particular siRNA selected to silence a target mRNA. The cell-penetrating peptides according to the invention can also be used to deliver a mix of several different siRNA, with an improved inhibiting activity. microRNAs (miRNAs), selected for their ability to affect expression of genes and proteins that regulate cell proliferation and/or cell death, can also be complexed with VEPEP-9. In another preferred embodiment of the complex according to the invention, the cargo is a small molecule (size lower that 1.5 kDa), preferably hydrophobic, either hydrophobic or charged. Preferred cargos in the complexes according to the present invention are anticancer and antiviral drugs. Non-limitative examples of small hydrophobic molecules which can be used include amino acid, di or tri peptide (labelled or not) daunomycin, Paclitaxel, doxorubicin, AZT, porphyrin, fluorescently-labelled-nucleosides or nucleotides (FAM-Guanosine, CY5_UTP, CY3-UTP), hydrophobic maghemite (contrast agents or magnetic nanoparticles Fe₂O₃) and fluorescent dyes.

The size of the complexes described above is preferably between 50 and 300 nm, more preferably between 50 and 200 nm (the size of the complex herein designates its mean diameter).

In the complexes according to the invention, the cargo/VEPEP-9 molar ratio depends on the nature and size of the cargo, but is generally comprised between 1/1 and 1/50. For small peptide or oligonucleotide cargoes, the cargo/VEPEP-9 molar ratio preferably ranges from 1/5 to 1/20. For small molecule cargoes, the cargo/VEPEP-9 molar ratio preferably ranges from 1/3 to 1/10.

According to an advantageous embodiment of the complexes as described above, the VEPEP-9 peptides comprise a polyethylene glycol group or an acetyl group covalently linked to their N-terminus, and/or a cysteamide group covalently linked to their C-terminus.

The above complexes can be advantageously used as "core shells" for obtaining bigger complexes, or nanoparticles, by an additional step of coating the cargo/VEPEP-9 complex with another layer of cell-penetrating peptides, which can be different from the VEPEP-9 peptides described above. Examples of such nanoparticles are VEPEP-9/CADY (wherein CADY is a CPP as described in EP1795539 and in [11]), VEPEP-9/PEP-1 (wherein Pep-1 is a CPP as described in [8]), VEPEP-9/MPG (wherein MPG is a CPP as described in U.S. Pat. No. 7,514,530 and in [7, 10]), as well as nanoparticles covered by a CPP belonging to another VEPEP family, for example selected from the following list:

```
VEPEP-3a:                           (SEQ ID No: 25)
Ac-X₁KWFERWFREWPRKRR-cysteamide VEPEP-3b:                           (SEQ ID No: 26)
Ac-X₁KWWERWWREWPRKRK-cysteamide VEPEP-3c:                           (SEQ ID No: 27)
Ac-X₁RWWEKWWTRWPRKRK-cysteamide, VEPEP-3d:                           (SEQ ID No: 28)
Ac-X₁RWYEKWYTEFPRRRR-cysteamide, VEPEP-3e:                           (SEQ ID No: 29)
Ac-X₁RWWRLWWRSWFRLWRR-cysteamide VEPEP-3f:                           (SEQ ID No: 30)
Ac-X₁LWWRRWWSRWWPRWRR-cysteamide
```

-continued

```
VEPEP-3g:                              (SEQ ID No: 31)
Ac-X₁LWWSRWWRSWFRLWFR-cysteamide, VEPEP-3h:                              (SEQ ID No: 32)
Ac-X₁KFWSRFWRSWFRLWRR-cysteamide, VEPEP-6a:                              (SEQ ID No: 33)
Ac-X₁LFRALWRLLRSLWRLLWK-cysteamide VEPEP-6b:                              (SEQ ID No: 34)
Ac-X₁LWRALWRLWRSLWRLLWKA-cysteamide VEPEP-6c:                              (SEQ ID No: 35)
Ac-X₁LWRALWRLLRSLWRLWRKA-cysteamide VEPEP-6d:                              (SEQ ID No: 36)
Ac-X₁LWRALWRLWRSLWRLWRKA-cysteamide VEPEP-6e:                              (SEQ ID No: 37)
Ac-X₁LWRALWRLLRALWRLLWKA-cysteamide VEPEP-6f:                              (SEQ ID No: 38)
Ac-X₁LWRALWRLLRNLWRLLWKA-cysteamide, VEPEP-3bstapl:                         (SEQ ID No: 39)
Ne-X₁KR_SWWERWWR_SSWPRKRK-cysteamide VEPEP-3estapl:                         (SEQ ID No 40)
Ac-X₁RWWR_SLWWRSWS_SRLWRR-cysteamide ST-VEPEP-6a:                           (SEQ ID No: 41)
Ac-X₁LFRALWR_SLLRS_SLWRLLWK-cysteamide ST-VEPEP-6aa:                          (SEQ ID No: 42)
Ac-X₁LFLARWR_SLLRS_SLWRLLWK-cysteamide ST-VEPEP-6ab:                          (SEQ ID No: 43)
Ac-X₁LFRALWS_SLLRS_SLWRLLWK-cysteamide ST-VEPEP-6ad:                          (SEQ ID No: 44)
Ac-X₁LFLARWS_SLLRS_SLWRLLWK-cysteamide ST-VEPEP-6b:                           (SEQ ID No: 45)
Ac-X₁LFRALWRLLR_SSLWS_SLLWK-cysteamide ST-VEPEP-6ba:                          (SEQ ID No: 46)
Ac-X₁LFLARWRLLR_SSLWS_SLLWK-cysteamide ST-VEPEP-6bb:                          (SEQ ID No: 47)
Ac-X₁LFRALWRLLS_SSLWS_SLLWK-cysteamide ST-VEPEP-6bd:                          (SEQ ID No: 48)
Ac-X₁LFLARWRLLS_SSLWS_SLLWK-cysteamide
ST-VEPEP-6c:                           (SEQ ID No: 49)
Ac-X₁LFAR_SLWRLLRS_SLWRLLWK-cysteamide,
``` as well as variants thereof (regarding the amino acid sequence and/or the N- and C-terminal chemical groups), wherein $X_1$ is beta-A or S and wherein the residues followed by an inferior "s" are linked by a hydrocarbon linkage. Preferred variants of the above sequences for forming nanoparticles according to the invention are PEGylated at their N-terminal extremity instead of acetylated.

Another aspect of the present invention pertains to nanoparticles made of a "core shell" comprising a cargo and a first carrier molecule, surrounded by VEPEP-9 peptides. These are herein referred to as "NANOPEP-9" particles. NANOPEP-9 technology constitutes a "custom-built" delivery system containing a common core particle, trapping therapeutic molecules, with surface VEPEP-9 peptides which are preferably functionalized for tumour or tissue targeting in vivo. From a structural point of view, NANOPEP-9 particles are constituted by a "core" which is coated by a layer of VEPEP-9 peptides. The "core" corresponds to a complex comprising a cargo and a vector or carrier such as a first cell-penetrating peptide, a liposome, a polycationic structure, a carbon nanoparticle, etc. In NANOPEP-9 particles, the layer of VEPEP-9 peptides (peripheral peptide) stabilizes the particle and can be functionalized. Functionalizing NANOPEP-9 particle surface with either cholesterol, lipid, PEG-molecules etc. improves particles stability in vivo, favours their administration by either systemic or topical routes and allows rapid liberation of active cargoes within tumor cells or tissues. Functionalization of the surface of NANOPEP-9 particles with small FAB fragments, peptides, antibodies and lipids has been shown to favour in vivo tissue or tumour targeting. Also, functionalizing NANOPEP-9 particle surface with polysaccharide such as PLGA, can be used as formulation for slow release of drug and cargo and allow a long term response in vivo. As shown in Example 5 below, the inventors have observed that N-terminal PEGylation of at least part of the VEPEP-9 peptides surrounding the NANOPEP-9 particles increases the biodistribution of cargoes in the tumour (10 to 20-fold increase), probably by stabilizing the NANOPEP-9 particles in the plasma.

NANOPEP-9 technology improves both cellular and in vivo delivery of biologically active cargoes and has been validated on a large set of cell lines including adherent and suspension cell lines, hard to transfect cell lines. NANOPEP-9 particles strongly interact with cell membranes and enter the cell independently of the endosomal pathway or rapidly escape from early endosomes. NANOPEP-9 technology presents several advantages including rapid delivery with very high efficiency, stability in physiological buffers, protection of the cargo against degradation, lack of toxicity and of sensitivity to serum, ability of forming mix nanoparticles, can be functionalized and have been successfully applied to the delivery of different types of cargoes into a large variety of cell lines as well as in animal models, thereby constituting powerful tools for basic research and therapeutic applications. NANOPEP-9 technology can be applied both at therapeutic and diagnostic/theragnostic levels.

In a particular embodiment of NANOPEP-9 particles according to the present invention, the cargo is complexed to a first cell-penetrating peptide, which can be for example, selected amongst CADY, MPG, PEP-1, PPTG1, poly Arginine motif, VEPEP-family peptides (VEPEP-3, VEPEP-6, VEPEP-9, stappled-VEPEP-6 or VEPEP-3) peptides described above (such as SEQ ID Nos: 1 to 10 and 25 to 49 and variants thereof), or any other known CPP. This cargo/CPP complex is then coated with a layer of VEPEP-9 peptides. According to this embodiment, the skilled artisan will advantageously choose the first CPP depending on the nature of the cargo, so that the complex of cargo and first CPP is stable. Hence, a wide diversity of cargoes can be included in NANOPEP-9 particles.

In the nanoparticles as above-described, the core/VEPEP-9 molar ratio depends on the nature and size of the core, but is generally comprised between 1/1 and 1/50. For small peptide/CPP cores, the core/peripheral VEPEP-9 molar ratio preferably ranges from 1/5 to 1/30, depending on the nature of peptide cargo (hydrophobicity and charge).

In a preferred embodiment of the nanoparticles according to the invention, the size of the nanoparticle is between 20 and 300 nm.

According to an advantageous embodiment of the NANOPEP-9 particles according to the invention, at least part of the VEPEP-9 peptides forming the peripheral layer of the nanoparticles comprise a poly-ethylene glycol or an acetyl group covalently linked to their N-terminus, and/or a cysteamide group covalently linked to their C-terminus.

According to another preferred embodiment, the core shell of the particles is coated with a VEPEP-9 peptide functionalized with NTA (for example, a VEPEP-9 peptide with nitrilotriacetic acid covalently linked to its C-terminus). This allows the subsequent attachment to the surface of the particle, of any protein (or other molecule) harbouring a histidine tag. This strategy offers the major advantage of having a common two-layer particles "NANOPEPHIS-9" that can be associated to any His-tagged molecule.

In particular embodiments of the complexes and nanoparticles according to the invention, at least part of the VEPEP-9 cell-penetrating peptides are bound to a targeting molecule. In the case of NANOPEP-9 particles, examples of targeting molecules include: antibodies, nanobodies and Fc or FAB fragments targeting HEK2, MUC1, EGF or XCCR4, as well as ligands, especially targeting receptors which are over-expressed at the surface of certain cell-types, horning peptides specific of selected organs. Non-limitative examples of such ligands and homing peptides are: RGD-peptide, homing targeting peptides (brain NT1 peptide. Ganglion GMI peptide, as well as all other previously described and selected peptide for tissues and cell line targeting), folic acid, polysaccharides, Matrix metalloprotease targeting peptide motif (MMP-9 or MMP3 for tumour selectivity).

According to a particular embodiment of the present invention, the complexes or nanoparticles are formulated so that they can be stored during several months without losing their stability and functional efficacy. As disclosed in example 5 below, the complexes and nanoparticles of the invention can advantageously be lyophilized in the presence of a sugar. Non-limitative examples of sugars which can be used to that aim are sucrose, glucose, manitol and a mix thereof, and they can be used, for example, in a concentration ranging from 5% to 20%, preferably 5% to 10%, it being understood that a concentration of 5% is obtained by adding 5 grams per liter of solution before lyophilization.

Another aspect of the present invention is the use of a complex or nanoparticle as above-described, as a medicament and as a marker or an imaging agent.

The present invention also pertains to a therapeutic, cosmetic or diagnostic composition comprising a complex or a nanoparticle as described above. For example, a composition comprising a complex or nanoparticle having a peptide targeting protein/protein interactions, involving essential protein CDK and Cyclin required for cell cycle progression as a cargo, and a targeting molecule specific for tumour cells (for example: RGD-peptide, folic acid, MUC-1 or HEK2 antibodies or nanobodies), is part of the present invention. Depending on the application, this composition can be formulated for intravenous, intratumoral, topical, intrarectal, intranasal, transdermal, or intradermal administration, or for administration via a mouth spray, or for administration as a subcutaneous implant for slow release of a drug.

The present invention also pertains to a method for delivering a molecule into a cell in vitro, comprising a step of putting said cell into contact with a complex or nanoparticle as described above.

Several aspects of the present invention are further developed in the following examples, illustrated by the figures (which are described in the examples).

EXAMPLES

Example 1

Materials and Methods

VEPEP-9 Peptides

All the peptides were synthesized by solid-phase peptide synthesis using AEDI-expensin resin with (fluorenyl-methoxy)-carbonyl (Fmoc) on a Pioneer Peptide Synthesizer (Pioneer™, Applied Biosystems, Foster City, Calif.) starting from Fmoc-PAL-PEG-PS resin at a 0.2 mmol scale. The coupling reactions were performed with 0.5 M of HATU in the presence of 1 M of DIEA. Protecting group removal and final cleavage from the resin were carried out with TFA/Phenol/$H_2O$/Thioanisol/Ethanedithiol (82.5/5/5/5/2.5%) for 3 h 30 min. All the peptides presented a cysteamide group at the C-terminus and were acetylated at the N-terminus. The peptide synthesis started by the C-terminus, using an AEDI-expensin resin starting with a cysteamide link, as described by Mery et al, 1992. All the peptides contained a beta-Alanine or a serine at the N-terminus to favour any further functionalization without using the C-terminal cysteamide group.

Functionalization of VEPEP-9

Two approaches were used for peptide functionalization (1) Peptide conjugations with peptide, antibody, PEGylation, NTA, cholesterol, stearylation, were performed at the primary amino group of the N-terminal residue, through a beta alanine or serine. It is advantageous to maintain the C-terminal cysteamide free, since it is known to be required to stabilize the particle through disulfide bounds (SH—SH). Functionalized peptides were further purified by Reverse Phase-HPLC and analyzed by electro-spray ionization mass spectroscopy.

(2) Peptide conjugations were also performed via disulfide bound using the SH-group of the cysteamide moiety of the peptide.

```
VEPEP-9-Funct-1:                           (SEQ ID No: 13)
X-LRWWLRWASRW(A-F)SRWAW(W-F)R-CH2-CH2-SH VEPEP-9-Funct-2:                           (SEQ ID No: 14)
Ac-LRWWLRWASRW(A-F)SRWAW(W-F)R-CH2-CH2-S-S-X VEPEP-9-Funct-3:                           (SEQ ID No: 15)
X-WWGSWATPRRRWWR-CH2-CH2-SH VEPEP-9-Funct-4:                           (SEQ ID No: 16)
Ac-WWGSWATPRRRWWR-CH2-CH2-S-S-X
```

X: Cholesterol, PEGylation, stearyl, palmitoyl, small FC or FAB fragments, nanobody, nitrilotriacetic acid (2×NTA), tissues targeting peptides (brain, lung, lymph node, pancreas . . . ).

VEPEP-9 Structure

VEPEP-9 peptides, except VEPEP-9c and VEPEP-9e, are secondary amphipatic peptides; they are highly versatile and show a strong structural polymorphism. VEPEP-9 are unfolded in solution as a free form and adopt an alpha helical conformation in the presence of lipid or artificial cellular membranes as well as in the presence of cargos such as peptide, SMH and small oligonucleotide (FIG. 1, wherein "H" stand for "helix" and "t" for "turn"). In contrast VEPEP-9c and VEPEP-9e adopt a coil/turn organization due to the presence of the proline residue in the sequence. The N-terminus domain of VEPEP-9c adopt an alpha helical conformation in the presence of lipid or artificial cellular membranes as well as in the presence of cargos.

Peptides

Peptides targeting CDK/Cyclin (C4: KKQVRMAHLVET (SEQ ID No: 50)) linear or cyclic version were obtained for Polypeptide. Fluorescently labelled (CY5 and CY3) tri (GWSC-dye (SEQ ID No: 51)) and tetra (GWASC-dye (SEQ ID No: 52)) peptides were also obtained for Polypeptide.

Oligonucleotides &siRNA siRNAs and 5' Alexa$^{700}$ or fluorescein (5'-FAM) fluorescently labelled siRNA were synthesized by Eurogentec (Belgium) according to the following sequences:

```
Cyc-B1 sense                    (SEQ ID No: 17)
5'GGCGAAGAUCAACAUGGCATT3'

Cyc-B1 antisense                (SEQ ID No: 18)
5'UGCCAUGUUGAUCUUCGCCTT3'

Cyc-B3 sense                    (SEQ ID No 19)
5'GGUGAAGAUCAGCAUGGCATT3'

Cyc-B3 antisense                (SEQ ID No: 20)
5'UGCCAUGUCGAUCUUCACCTT3'

GAPDH sense                     (SEQ ID No: 21)
5'CAUCAUCCCUGCCUCUACUTT-3'
and

GAPDH antisense                 (SEQ ID No: 22)
5'AGUAGAGGCAGGGAUGAUG3'
```

Short oligonucleotides and PNA were also obtained for Eurogentec:

```
ODN1:                           (SEQ ID No: 23)
AGCTTAGCTT-Cy5

Cyc-B1a;                        (SEQ ID No: 24)
TGCCATCGGGCTTGG-Cy5
```

Fluorescence Titrations

Fluorescence experiments were performed on a PTI spectrofluorimeter at 25° C. in a NaCl 154 mM buffer. Intrinsic Trp-fluorescence of VEPEP-9 was excited at 290 nm and emission spectrum was recorded between 310 and 400 nm, with a spectral band-pass of 2 and 8 nm for excitation and emission, respectively. FITC- or CY5-fluorescence of labelled-peptide or Oligonucleotide were excited at 492 nm and emission recorded between 500 and 580 nm. For VEPEP-9/peptide interaction, 0.5 µM of FITC-labelled peptide was titrated by increasing concentrations of VEPEP-9. For VEPEP-9/oligonucleotide interaction, 200 nM of FITC or CY5-labelled oligodeoxynucleotide (ODN) was titrated by increasing concentrations of VEPEP-9. All measurements were corrected for the dilution and curve fitting were performed by using Grafit software (Erithacus).

Characterization of Peptide-Based Nanoparticles

Mean particle size distribution was determined with a Coulter N4 Plus (Coulter-Beckman) at 25° C. for 3 min per measurement and zeta potential was measured with Zetasizer 4 apparatus (Malvern Ltd,)

Cell Culture and VEPEP-Mediated Cargo Delivery

Adherent HS68 fibroblasts, HeLa, PC3, MCF-7, SCK3-Her2, PBMC cell lines (from American Type Culture Collection (ATCC)) were cultured in Dulbecco's Modified Eagle's Medium supplemented with 2 mM glutamine, 1% antibiotics (streptomycin 10,000 µg/ml, penicillin, 10,000 IU/ml) and 10% (w/v) foetal calf serum (FCS), at 37° C. in a humidified atmosphere containing 5% $CO_2$. Stock solutions of VEPEP-9/peptide particles were prepared by complexing 1 µM peptide with VEPEP-9 peptides at a molar ratio of 1/20 for 30 min at 37° C. Lower concentrations of VEPEP-9-carrier/peptide (from 500 nM to 1 µM) were obtained by serial dilution of the stock complexes in PBS, in order to preserve the same VEPEP-9-carrier/peptide ratio. Stock solutions of VEPEP-9/siRNA particles were prepared by complexing 100 nM siRNA with VEPEP-9 peptides at a molar ratio of 1/20 for 30 min at 37° C. Lower concentrations of VEPEP-9/siRNA (from 20 nM to 0.125 nM) were obtained by serial dilution of the stock complexes in PBS, in order to preserve the same VEPEP-9/siRNA ratio. 150,000 cells seeded in a 35 mm dish the day prior transfection, were grown to 60% confluence and overlaid with 200 µl of preformed complexes, incubated for 3-5 min, then 400 µl of DMEM were added. After 30 min. incubation at 37° C., 1 ml of fresh DMEM containing 16% foetal calf serum (FCS) was added in order to reach a final FCS concentration of 10%, without removing the overlay of VEPEP-9/cargo complexes. Cells were returned to the incubator for 24 hrs. For cdk2 derived peptides, cell proliferation was monitored after 24 and 48 hrs. For siRNA targeting Cyclin B1, Cyclin B1 mRNA level was determined 24 hrs following transduction, using Quantigen (Panomics Inc.). Data reported are an average of 3 or 4 distinct experiments.

Cytotoxicity

Toxicity of VEPEP-9/peptide or VEPEP-9/ODN complexes was investigated on Hela and HS-68 cell lines. 30,000 cells seeded in 24-well plated the day prior transfection, were incubated with increasing concentrations of peptide or ODN complexed with VEPEP-9 at a 20/1 molar ratio ranging from 1 to 5 µM (500 µM VEPEP-9), for 30 min prior to addition of medium to reach a final 10% concentration of FCS. Cytotoxic response was measured 12 hr or 24 hr later by monitoring the housekeeping gene cyclophilin nRNA level (Quantigen, Panomic Inc.) and by colorimetric MTT assay (Sigma, Germany), respectively. For MTT assay, cell culture medium was removed and replaced with PBS containing 2.5 mg/ml of MTT for 4 hr. Results correspond to the average of 3 separate experiments.

Mouse Tumour Models

Athymic female nude mice (6-8 weeks of age) were subcutaneously inoculated into the flank with $1 \times 10^6$ PC3, A549 or SCK-3-HEK2 cells in 100 µl PBS.

For Peptide treatments: Two to three weeks after tumour implant, when tumour size reached about 100 mm$^3$ animals were treated by intratumoral or intravenous injection, every 3 days, with a solution of 0.1 ml of either free Cdk2 derived peptide (200 µg), control scramble peptide C2S (VTLMEAKKQVLT (SEQ ID No: 53)) or C2 (KKQV-LAMEHLVT (SEQ ID No: 54)) peptides (10, 50, 100 µg) complexed with NANOPEP-9 at a 1/20 molar ratio.

For small molecule treatments: Two to three weeks after tumour implant, when tumour size reached about 100 mm$^3$, animals were treated by intratumoral or intravenous injection, every 3 days, with a solution of 0.1 ml of either free daunomycine (1 mg), or daunomycine (0.1, 0.2 mg) complexed with NANOPEP-9 at a 1/30 molar ratio or formulations containing 15% PEG-NANOPEP-9 at the surface.

For siRNA treatment: Two to three weeks after tumour implant, when tumour size reached about 100 mm$^3$, animals were treated by intratumoral or intravenous injection, every 3 days, with a solution of 0.1 ml of either free Cyc-B1 siRNA (50 or 100 µg), control siRNA Cyc-B3 or Cyc-B1 siRNA (1, 5, 10 µg) complexed with NANOPEP-9 at a 1/20 molar ratio.

For PNA treatment: Two to three weeks after tumour implant, when tumour size reached about 100 mm$^3$, animals were treated by intratumoral or intravenous injection, every 3 days, with a solution of 0.1 ml of either free Cyc-B1PNA (50 or 100 µg), or Cyc-B1PNA (1, 5, 10 µg) complexed with NANOPEP-9 or NANOPEP-9/PEG-NANOPEP-9 at a 1/20 molar ratio. Formulations containing 15% PEG-NANO-PEP-9 were prepared in a stepwise fashion by first forming a precomplex of NANOPEP-9/PNA at molar ratio of 1/20, followed by addition of PEG-NANOPEP-9 so as to increase the ratio of PNA/carrier to 1/25.

Tumour diameter was measured in two directions at regular intervals using a digital calliper and tumour volume was calculated as length×width×height×0.52. Curves show the mean value of tumour size in a cohort of six animals and neither animal death nor any sign of toxicity were observed. Experiments were performed according to national regulations and approved by the local animal experimentation ethical committee. The statistical significance of the results was calculated by Student's t test and p<0.05 considered to be statistically significant.

In Vivo Imaging of Peptide/siRNA Biodistribution

In vivo fluorescence imaging was performed as previously described by Crombez et al, 2009, Nucleic acid res. [10]. Mice were injected intravenously with 100 µg (200 µl) of Alexa700 fluorescently labelled peptide (C4 or tetrapeptide: GWASC, SEQ ID No: 52)) or siRNA either naked or complexed with VEPEP-9 (n 4 animals per group). Anaesthetized mice, using 2% Isoflurane, were illuminated by 663 nm light emitting diodes equipped with interference filters and movies were acquired over the first 15 minutes and fluorescence images were taken every hour for 5 hrs and then after 24 hrs, with a back-thinned CCD cooled camera as previously described (Crombez et al, supra). At 24 hr, mice were euthanized and different organs were removed for quantification of Alexa fluorescence.

Example 2

VEPEP-9 Peptides Applications for Molecules Delivery

Example 2.1

VEPEP-9 Peptides Form Stable Nanostructures with Cargoes

VEPEP-9 peptide form stable complexes with peptides and ODN. The binding of cargos to VEPEP-9 was monitored by fluorescence spectroscopy using the both intrinsic Trp group of VEPEP-9 (3 to 5 Trp-residues) and extrinsic fluorescently labelled cargoes (using Cy3, Cy5 or FITC). Curve fitting reveal that VEPEP-9 strongly binds the different cargoes with dissociation constant in the nanomolar range (Tables 1 and 2 and FIG. 2).

VEPEP-9 peptides form stable particles with different cargoes including peptide, siRNA, PNA and small aromatic (FIG. 2). The dissociation constant for peptide, siRNA, PNA and small hydrophobic molecule ranges between 10-100 nM, 5-50 nM, 5-50 nM and 0.02 to 0.2 µM, respectively, depending on the nature of the dyes and of the cargoes.

TABLE 1

VEPEP-9/Cargo complexes characterization. Peptide (C4), siRNA, PNA (15 mer -PNA), and small hydrophobic molecule.

| | Cargoes | | | | | | | |
|---|---|---|---|---|---|---|---|---|
| | peptide | | siRNA | | PNA | | SHM | |
| VEPEP-9 | Binding | Kd (nM) | Binding | Kd (nM) | Binding | Kd (nM) | Binding | Kd (µM) |
| VEPEP-9a: | yes | 10-100 | yes | 5-50 | Yes | 5-50 | Yes | 0.02-0.1 |
| VEPEP-9b | yes | 10-100 | yes | 5-50 | Yes | 5-50 | Yes | 0.02-0.1 |
| VEPEP-9c: | yes | 10-100 | yes | 5-50 | Yes | 5-50 | Yes | 0.02-0.1 |
| VEPEP-9d: | yes | 10-100 | yes | >200 | Yes | >50 | Yes | 0.02-0.1 |
| VEPEP-9e | yes | 10-100 | yes | 5-50 | Yes | 5-50 | Yes | 0.02-0.1 |
| VEPEP-9f: | yes | 10-100 | yes | >200 | Yes | >50 | Yes | 0.02-0.1 |

Binding of small molecule cargoes has been investigated in detailed depending on the nature of the SHM. Several hydrophobic molecules have been used (Daunomycin, Paclitaxel, doxorubicin, porphyrin), as well as charged molecules (nucleotide, nucleoside and fluorescent dyes).

TABLE 2

VEPEP-9/Cargo complexes characterization.

| | Cargoes | | | | | | | |
|---|---|---|---|---|---|---|---|---|
| | Doxorubicin | | porphyrin | | AZT | | FAM-guanosine | |
| VEPEP-9 | Binding | Kd (µM) | Binding | Kd (µM) | Binding | Kd (µM) | Binding | Kd (µM) |
| VEPEP-9a: | yes | 0.02 | yes | 0.4 | yes | 0.4 | yes | 0.02 |
| VEPEP-9b | yes | 0.07 | yes | 0.5 | yes | 0.5 | yes | 0.3 |
| VEPEP-9c: | yes | 0.01 | yes | 0.08 | yes | 0.03 | yes | 0.09 |
| VEPEP-9d: | yes | 0.09 | yes | 0.25 | yes | 0.02 | yes | 0.4 |
| VEPEP-9e | yes | 0.05 | yes | 0.20 | yes | 0.09 | yes | 1.1 |
| VEPEP-9f: | yes | 0.01 | yes | 0.11 | No | — | yes | 0.8 |

SHM: small hydrophobic molecules (porphyrin, FAM-G, AZT, doxorubicin)

Example 2.2

VEPEP-9 Peptides Form Stable Nanoparticles with their Different Cargoes

Figure 3:
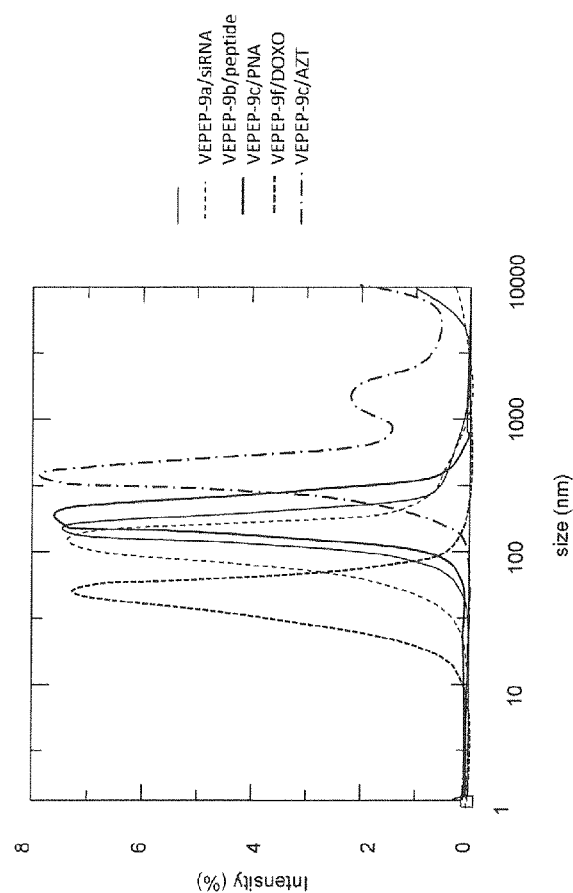
FIG. 3 shows the particle size distribution of several VEPEP-9/cargo complexes (VEPEP-9a/siRNA, VEPEP-9b/peptide, VEPEP-9c/PNA, VEPEP-9f/Doxo, and VEPEP-9c/AZT) at cargo/VEPEP-9 molar ratio of 1/20 (as determined by dynamic light scattering).

The size of the particles was monitored by dynamic light scattering. For all the VEPEP-9 peptides, optimal VEPEP-9 peptide/cargo molar ratio is ranging between 1/5 to 1/30 (FIG. 3). The size of the particles is of about 50 to 200 nanometer in diameter.

Example 3

VEPEP-9 Applications in Cultured Cells

Example 3d

VEPEP-9 Mediated Delivery of Peptide and siRNA in Different Cell Lines

VEPEP-9 peptides have been used for the delivery of different peptides and siRNA into different cell lines, including primary cell lines, stem cell lines and challenging cell lines. Peptide or siRNA delivery was monitored using two approaches: fluorescence spectroscopy and by monitoring biological responses (anti proliferation, siRNA related knockdown).

Figure 4:
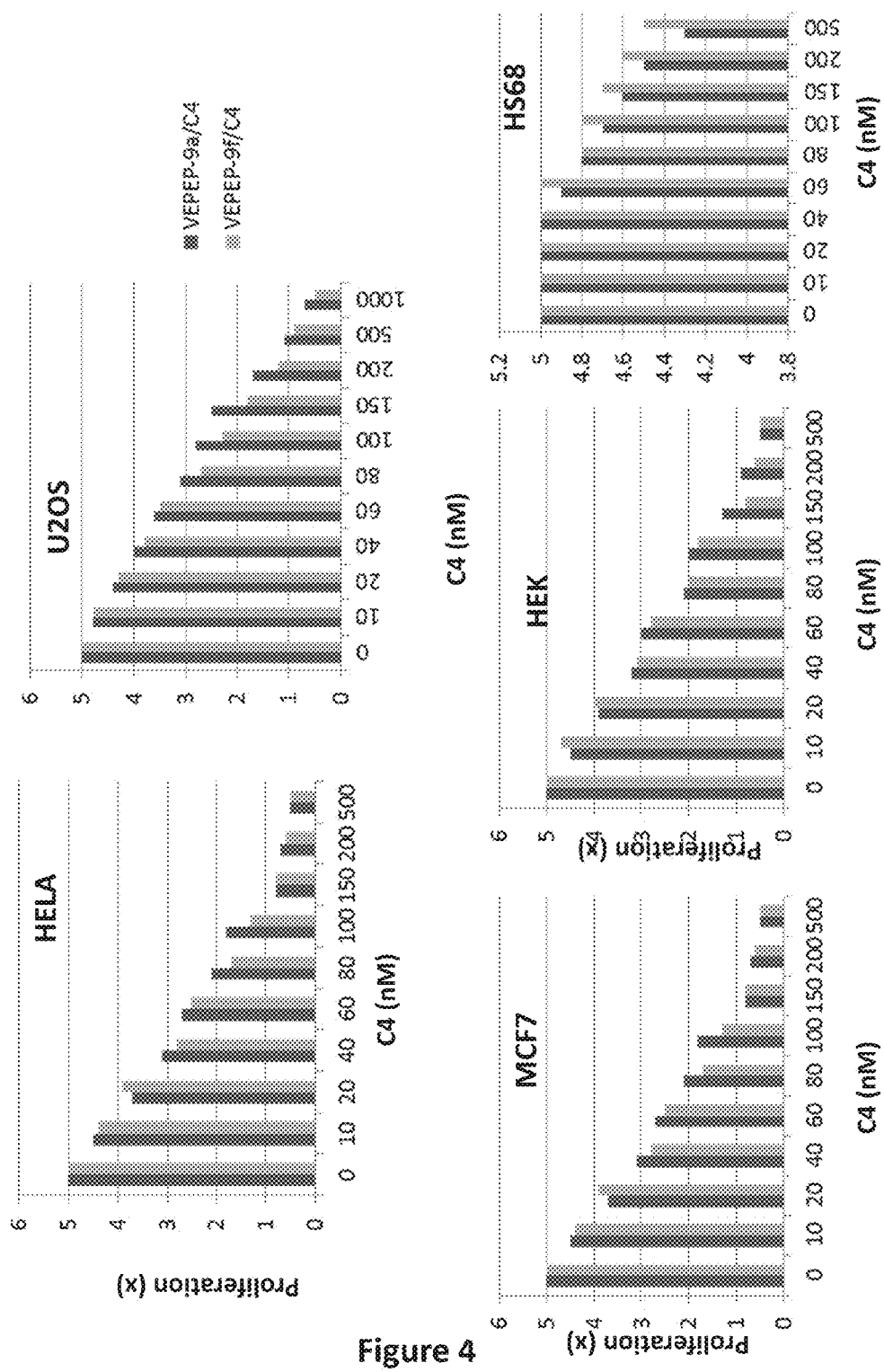
FIG. 4 shows the dose-response of VEPEP-9-mediated delivery of C4 peptides on proliferation in Hela, MCF7, HEK, HS-68, and U2OS cells. VEPEP-9a or VEPEP-9f peptides were used for C4 delivery.

1—Fluorescent labelled peptide was visualized in the different cell lines using fluorescence microscopy or FACS sorting (Table 3). In most of the cell lines, the uptake of Cy-5 labelled peptides is more than 70% of the cells 2—Dose-response experiments performed on different cultured cells revealed that VEPEP-9-mediated delivery of C4 peptides, targeting cdk2/cyclin A complex, block cell proliferation of different cancer cells (FIG. 4).

3—Dose-response experiments performed on different cultured cells revealed that VEPEP-9-mediated delivery of siRNA (GAPDH) induced a robust downregulation of GAPDH mRNA level (Table 3). In most of the cell lines, knockdown (KO) higher than 70% was obtained at the protein level.

| Cell lines | origin | Efficiency FACS Cy-5 C4 | Efficiency KO GAPDH |
|---|---|---|---|
| Hela | Human epithelial cervical cancer cells | 70% | 90% |
| STEM-CE | Mouse embryonic stem cells | 70% | 65% |
| Jurkat | Human T lymphocyte | 90% | 90% |
| HcpG2 | Human hepatocyte | 70% | 70% |
| C2C12 | Mouse myoblast | 80% | 90% |
| MEF | Mouse fibroblast | 75% | 80% |
| HS-68 | Human fibroblast | 90% | 80% |
| CEM-SS | Human macrophage | 60% | 70% |
| U2OS | Human osteoblast | 91% | 91% |
| MCF7 | Human breast adenocarcinoma | 70% | 70% |
| MT4 | Human T lymphocyte | 75% | 70% |
| HER2 | Human breast cancer | 90% | 90% |
| MDA-MB | Human breast cancer | 70% | 70% |
| PBMC | Human macrophage | 90% | 90% |

Example 3.2

VEPEP9-Mediated Delivery of Peptide Targeting Cdk2/Cyclin A or siRNA Targeting Cyclin B1 Induces G2 Arrest and Blocks Cancer Cell Proliferation Dose-response experiments performed on cultured cells revealed that VEPEP-9 mediated delivery of C4 peptide and siRNA (targeting cyclin B1: Cyc-B1) induced a robust biological response associated with specific cell cycle arrest in G2.

Figure 5:
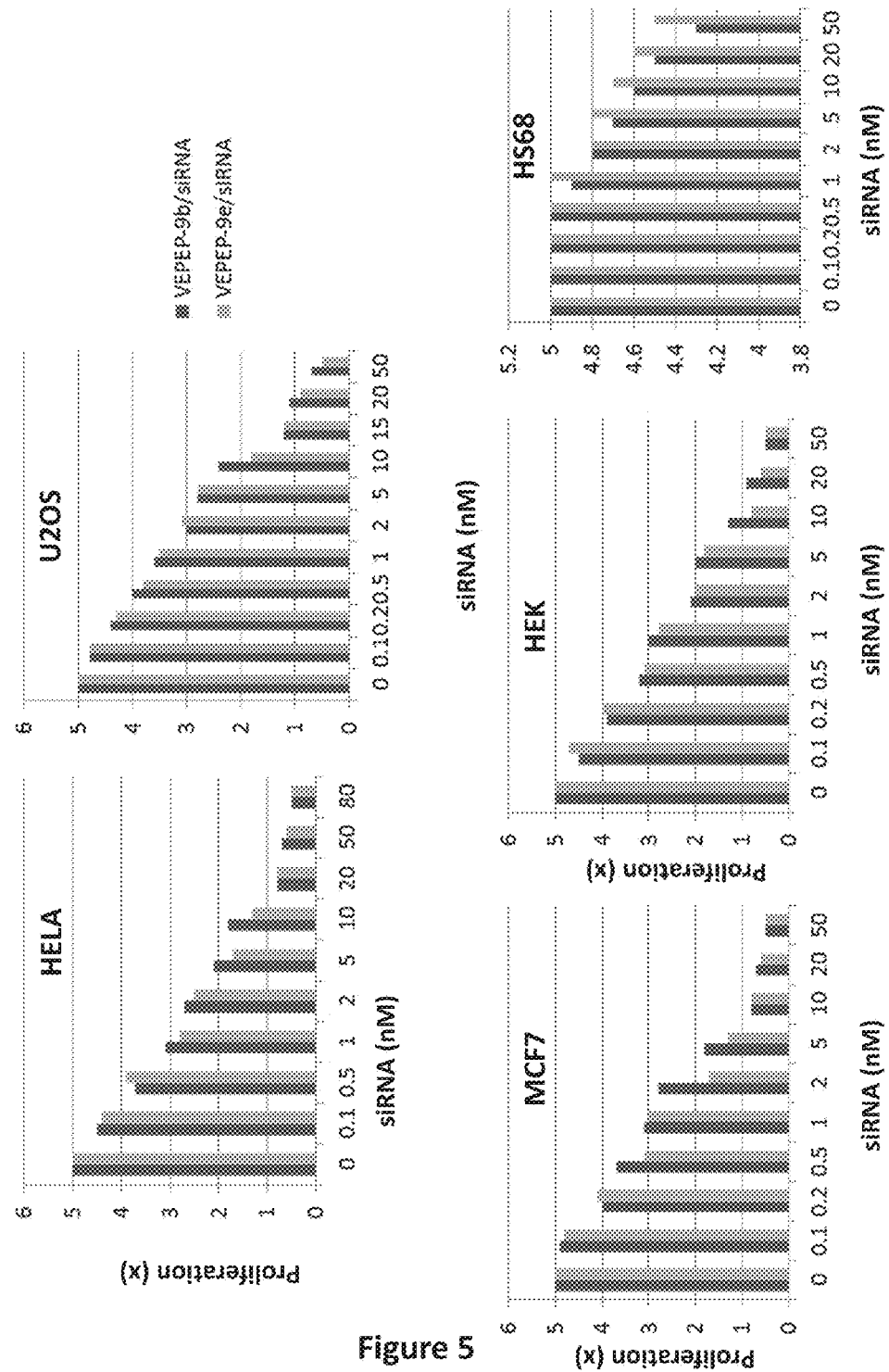
FIG. 5 shows the dose-response of VEPEP-9-mediated delivery of siRNA targeting Cyclin B1 on proliferation in Hela, MCF7, HEK, HS-68, and U2OS cells. VEPEP-9b or VEPEP-9e peptides were used for siRNA delivery.

For peptide delivery, VEPEP-9a and VEPEP-9f vectors were used. A C4 peptide concentration of 200 nM was sufficient to block proliferation of Hela, MCF7, HEK-2 and U2OS cells. $IC_{50}$ of 45±20 nM and 56±12 nM were estimated on Hela and MCF7, respectively. For siRNA delivery, VEPEP-9b and VEPEP-9e were used. A siRNA concentration of 20 nM was sufficient to block proliferation of Hela, MCF7, HEK-2 and U2OS cells. $IC_{50}$ of 3.1±0.2 nM, 1.6±0.5 nM and 4.2±1; 2 nM were estimated on Hela, MCF7 and HEK-2 respectively. In contrast, for both siRNA and C4 delivery proliferation was only reduced by 10% for non-transformed HS68 fibroblasts (FIG. 5), in perfect agreement with the impact of the check point G2-M on the cell cycle proliferation and showing the specificity of the peptide for cancer cells.

Figure 6:
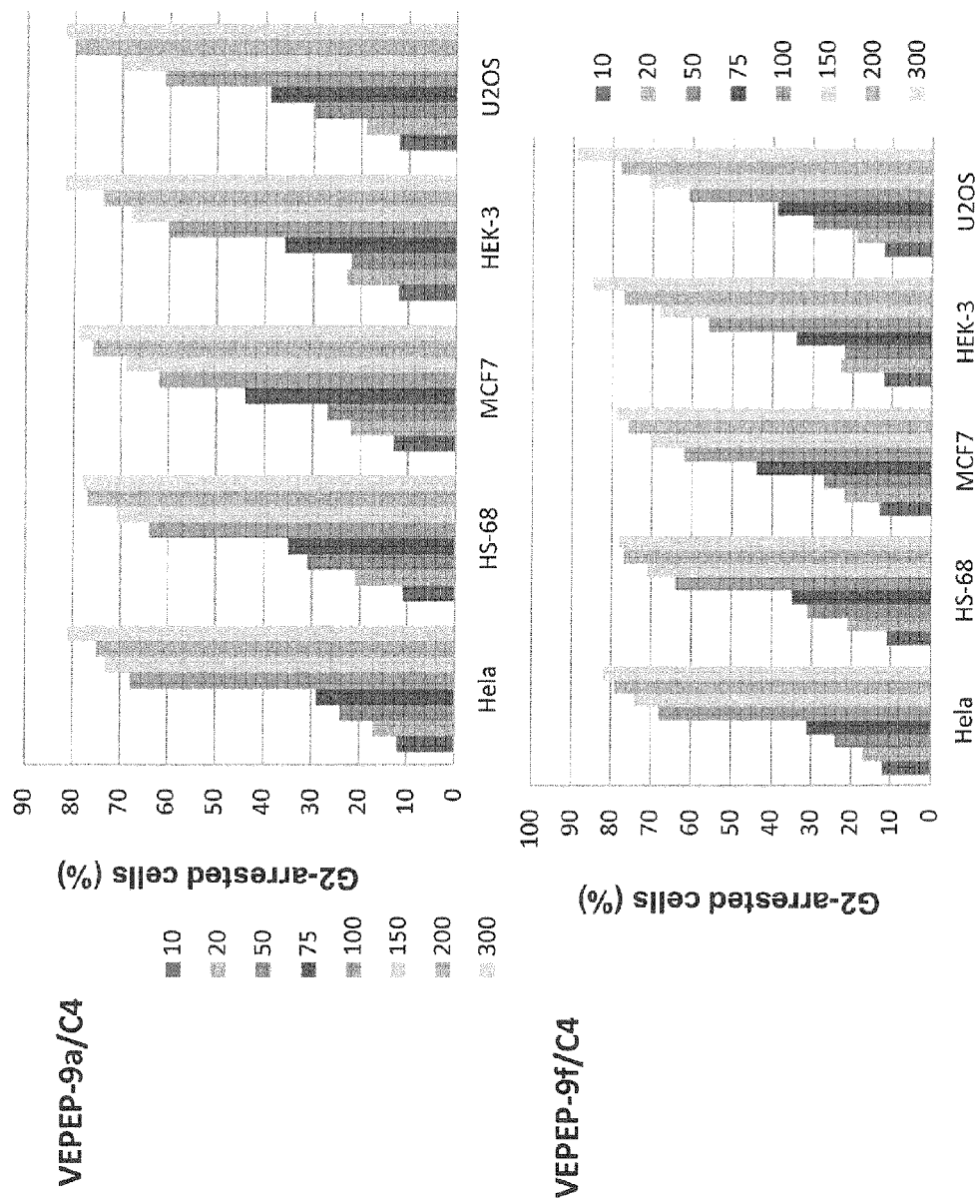
FIG. 6 shows the dose-response of VEPEP-9-mediated delivery of C4 peptides on G2 arrest in Hela, MCF7, HEK, HS-68, and U2OS cells. VEPEP-9a or VEPEP-9f peptides were used for C4 delivery.

C4 mediated dissociation of CDK2/cyclin A complex was directly associated with accumulation of cells with a 4N content, consistent with downregulation of Cdk1-Cyclin B1 activity, and was optimally obtained with 200 nM peptide and $IC_{50}$ values estimated to 42±12 nM and 52±15 nM for HeLa and MCF7 cells, respectively (FIG. 6). In contrast, no effect on cell cycle progression was observed with 500 nM of a scrambled C4 peptide, complexed with VEPEP-9 at a 20/1 ratio, or with VEPEP-9a or VEPEP-9f carrier alone (200 µM).

Figure 7:
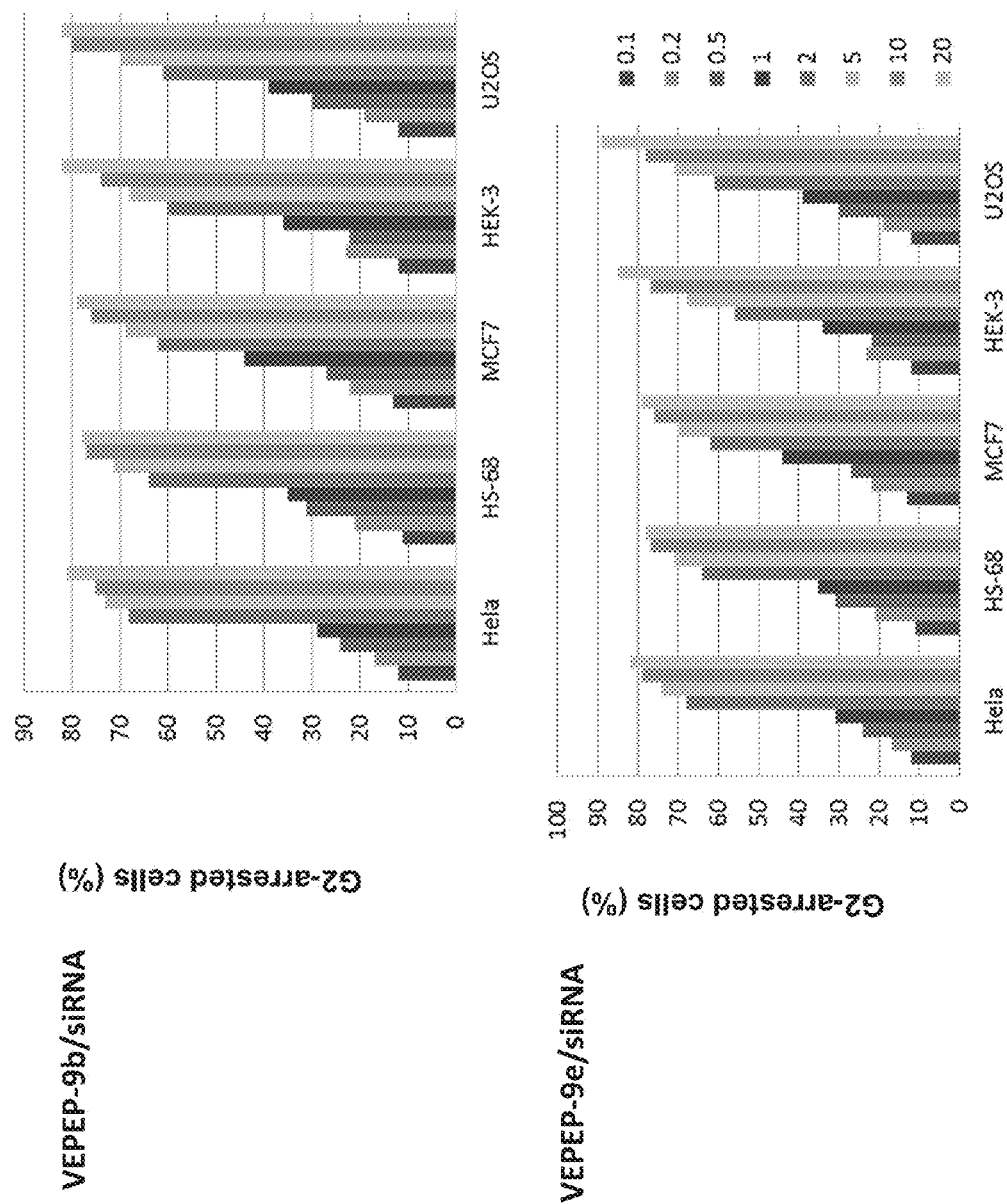
FIG. 7 shows the dose-response of VEPEP-9-mediated delivery of siRNA targeting Cyclin B1 on G2 arrest in Hela, MCF7, HEK, HS-68, and U2OS cells. VEPEP-9b or VEPEP-9e peptides were used for siRNA delivery.

SiRNA-mediated reduction of cyclin B1 protein levels was directly associated with accumulation of cells with a 4N content, consistent with downregulation of Cdk1-Cyclin B1 activity, and was optimally obtained with 20 nM siRNA and $IC_{50}$ values estimated to 2.4±0.8 nM, 1.9±0.9 nM and 1.2±0.6 nM for HeLa, MCF7 and HEK-2 respectively (FIG. 7). In contrast, no effect on cyclin B1 levels and cell cycle progression was observed with 200 nM of an unrelated siRNA (si-GAPDH), or of a mismatch siRNA harbouring two mutations (Cyc-B3) complexed with VEPEP-9 at a 20/1 ratio, or with VEPEP-9b and VEPEP-9e carrier alone (100 µM).

Example 3.3

VEPEP-9 Mediated Delivery of Small Peptides in Different Cell Lines

VEPEP-9a, VEPEP-9c and VEPEP-9f have been used for the delivery of small peptides into different cell lines, including primary cell lines, stem cell lines and challenging cell lines. Cargoes uptake was monitored using fluorescence spectroscopy and FACS analysis. Fluorescently labelled peptides were visualized in the different cell lines using fluorescence microscopy or FACS sorting (Table 4). In most of the cell lines, the uptake of Cy-5 labelled peptide is more than 70% of the cells.

| Cell lines | origin | Efficiency VEPEP-9a | Efficiency VEPEP-9c | Efficiency VEPEP-9f |
|---|---|---|---|---|
| Hela | Human epithelial cervical cancer cells | 70% | 80% | 60% |
| Jurkat | Human T lymphocyte | 65% | 57% | 65% |
| SEM | Mouse embryonic stem cells | 51% | 87% | 76% |
| HepG2 | Human hepatocyte | 71% | 75% | 48% |
| C2C12 | Mouse myoblast | 59% | 90% | 57% |
| MEF | Mouse fibroblast | 65% | 65% | 75% |
| HS-68 | Human fibroblast | 77% | 81% | 67% |
| CEM-SS | Human macrophage | 52% | 80% | 87% |
| U2OS | Human osteoblast | 79% | 78% | 57% |
| MCF7 | Human breast adenocarcinoma | 67% | 72% | 89% |
| MT4 | Human T lymphocyte | 52% | 47% | 56% |

Example 3.4

VEPEP9-Mediated Delivery of Peptide and ODN is not Toxic

Figure 8:
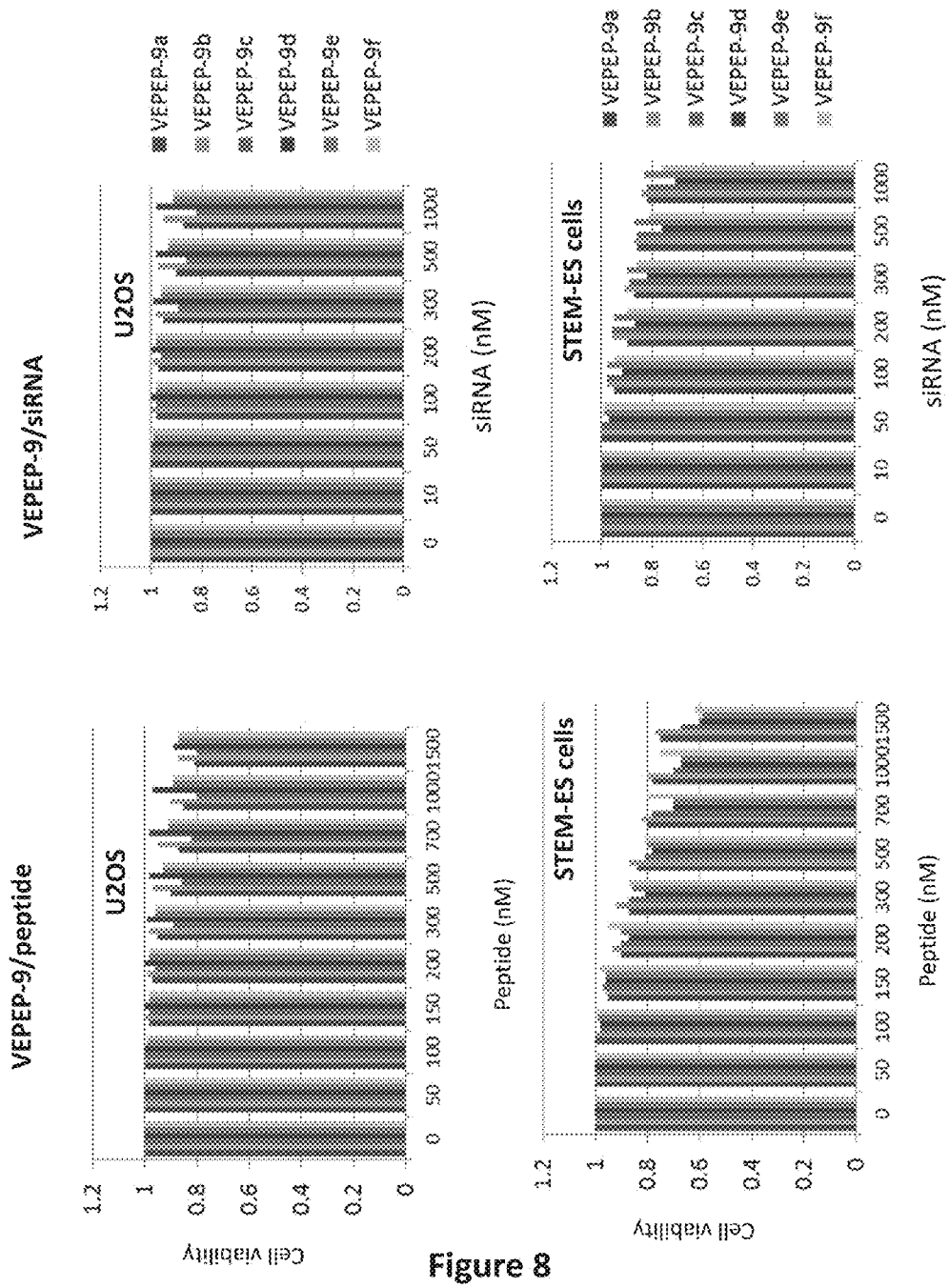
FIG. 8 shows the toxicity profile of VEPEP-9 particles on U2OS and STEM-ES cells (as determined by MTT assay and by cyclophilin mRNA level). VEPEP-9a, VEPEP-9b, VEPEP-9c, VEPEP-9d, VEPEP-9e, and VEPEP-9f peptides were complexed with either peptide or siRNA.

As shown on FIG. 8, the toxicity of VEPEP-9 particles was investigated on HeLa, U2OS and STEM ES cells by MTT assay and by monitoring the level of cyclophilin mRNA measured by Quantigen™ technology (Affymetrix). No toxicity was detected at levels up to 200 nM, and only a mild toxicity was observed at the maximum concentration of 1 µM.

Example 3.5

VEPEP-9 Mediated Delivery of PNA Molecule in Different Cell Lines

VEPEP-9 peptides have been used for the delivery of nucleic acid analogues (PNA and morpholino) into different cell lines, including primary cell lines and challenging cell lines. We demonstrated that VEPEP-9a, VEPEP-9c and VEPEP-9f form stable complexes with small PNA or morpholino oligonucleotides of 15 mer and have used them for the delivery of PNA into different cell lines, including primary cell lines, stem cell lines and challenging cell lines. Uptake was monitored using fluorescence spectroscopy and following biological response (Cyclin B1 knockdown).

Fluorescently labelled PNA was visualized in the different cell lines using fluorescence microscopy or FACS sorting (Table 5). In most of the cell lines, the uptake of Cy-5 labelled PNA is more than 60% of the cells.

| Cell lines | origin | Efficiency VEPEP-9a | Efficiency VEPEP-9c | Efficiency VEPEP-9f |
|---|---|---|---|---|
| Hela | Human epithelial cervical cancer cells | 67% | 82% | 78% |
| Jurkat | Human T lymphocyte | 55% | 77% | 81% |
| SEM | Mouse embryonic stem cells | 72% | 76% | 88% |
| HepG2 | Human hepatocyte | 81% | 84% | 71% |
| C2C12 | Mouse myoblast | 65% | 89% | 69% |
| MEF | Mouse fibroblast | 60% | 76% | 74% |
| HS-68 | Human fibroblast | 87% | 91% | 71% |
| CEM-SS | Human macrophage | 47% | 67% | 78% |
| U2OS | Human osteoblast | 64% | 71% | 89% |
| MCF7 | Human breast adenocarcinoma | 78% | 78% | 83% |
| MT4 | Human T lymphocyte | 76% | 54% | 67% |

Figure 9:
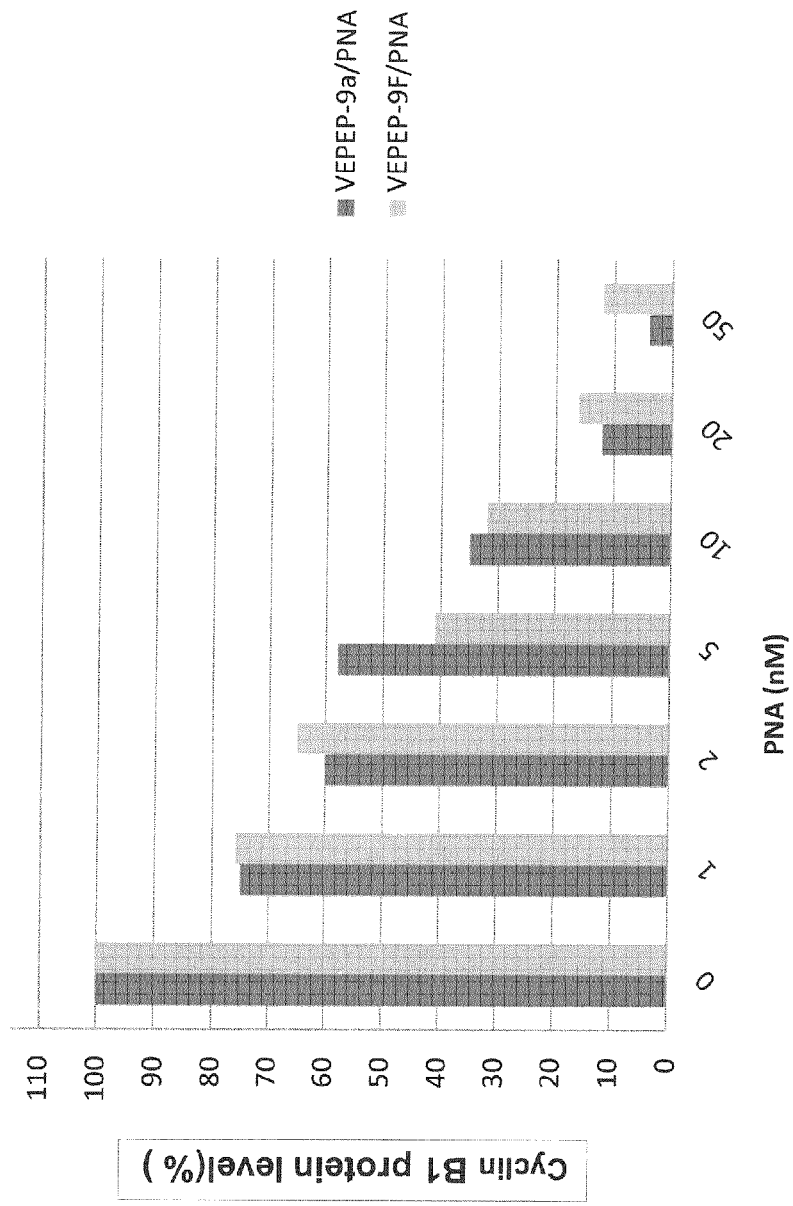
FIG. 9 shows the dose-response of VEPEP-9-mediated delivery of a Cyclin B1 antisense peptide nucleic acid (PNA) on Cyclin B1 protein levels in cells. VEPEP-9a and VEPEP-9f peptides were used for PNA delivery.

We then have applied VEPEP-9a and VEPEP-9f strategy for the delivery of PNA antisense targeting Cyclin B1 as previously described (Morris et al, 2007). Dose-response experiments performed on different cultured cells revealed that VEPEP-9-mediated delivery of PNA (Cyclin B1) induced a robust downregulation higher than 70% of Cyclin B1 protein level in Hela and MCF7 cells and no change in Cyclin B1 level was observed with free PNA and scrambled PNA molecule complexed with VEPEP-9 carrier (FIG. 9).

Example 3.6

Figure 10:
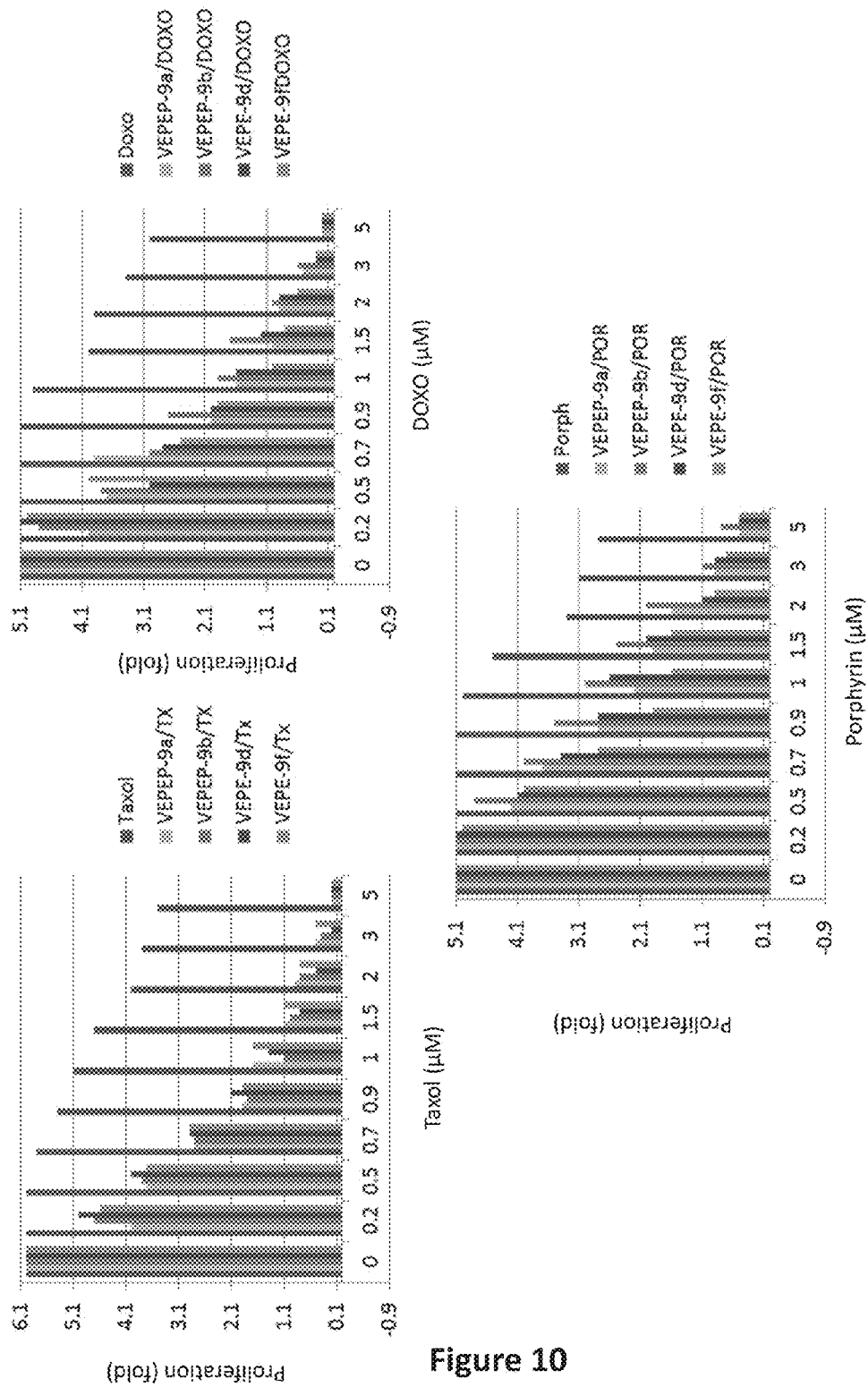
FIG. 10 shows the dose-response of VEPEP-9-mediated delivery of doxorubicin (Doxo), porphyrin (POR), or taxol (TX) on cancer cell proliferation. VEPEP-9a, VEPEP-9b, VEPEP-9d, and VEPEP-9f peptides were used for delivery in MCF-7 and SCK-3-HEK2 cells.
Figure 11:
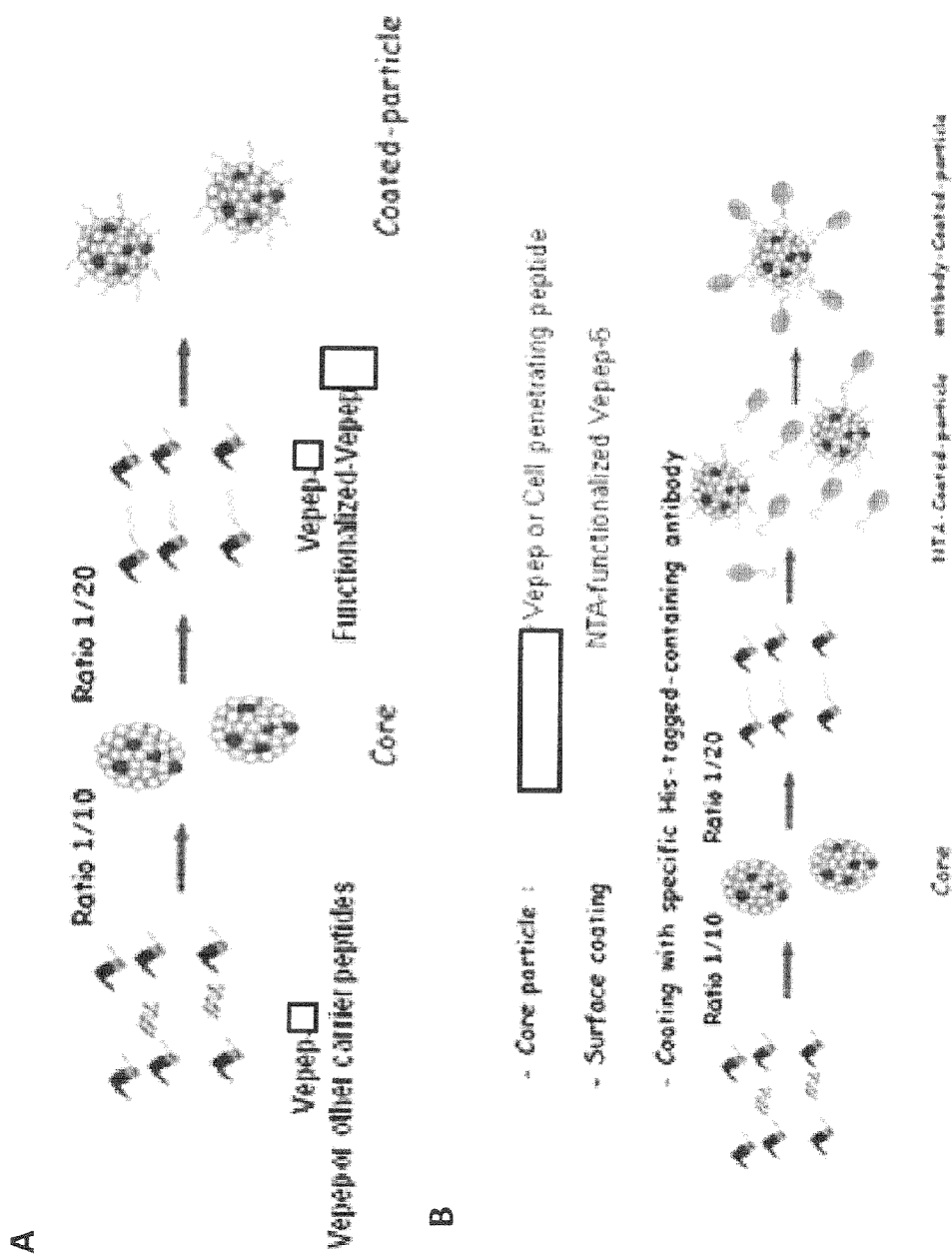
FIGS. 11A and 11B show schematics for the formation of NANOPEP particles having multilayer organization.
Figure 12:
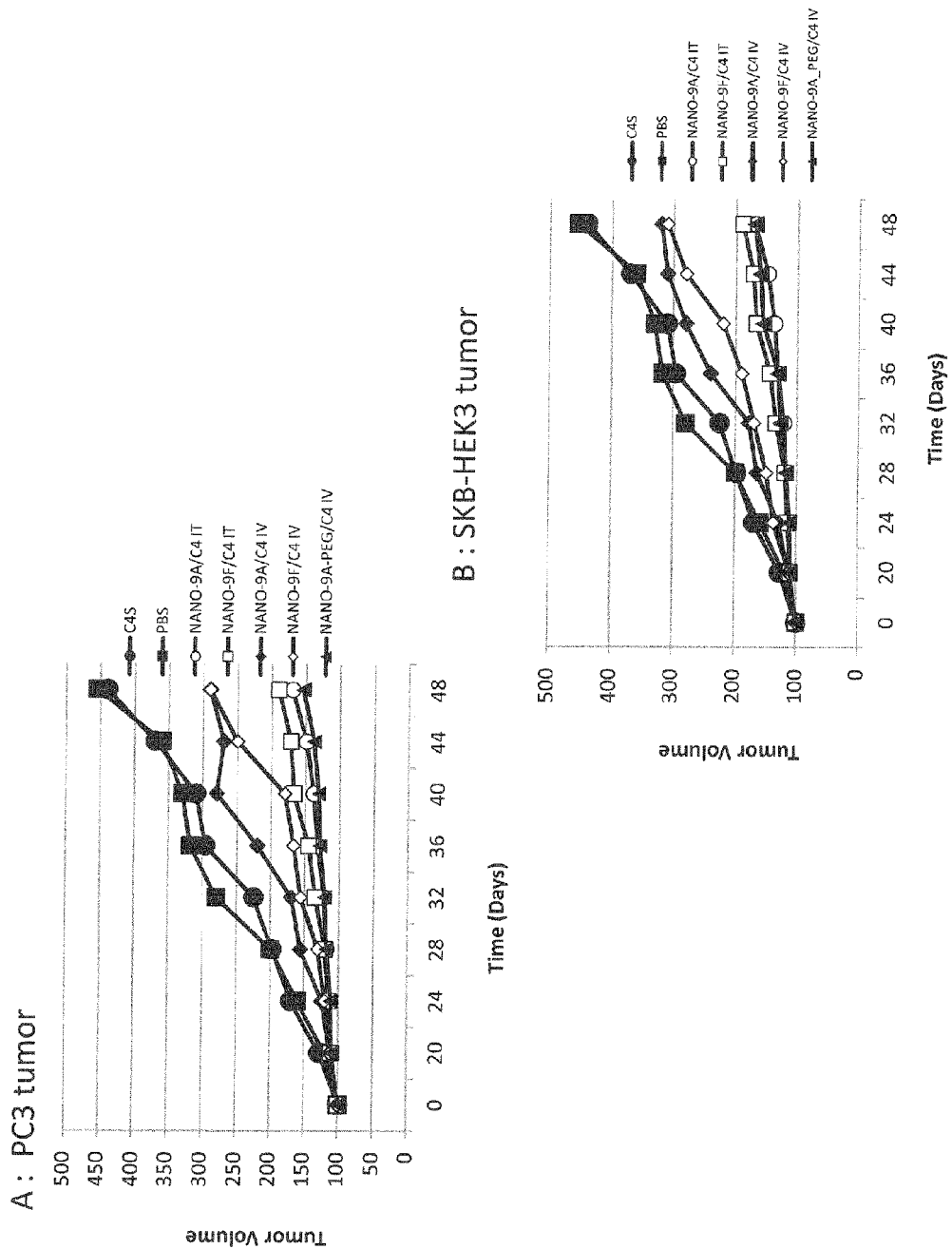
FIGS. 12A and 12B show reduction of tumor growth by intratumoral (IT) or intravenous (IV) administration of NANOPEP particles containing C4 peptide in PC3 (12A) or SKB-HEK3 (12B) xenograft mice. NANO-9A/C4: VEPEP-9a/C4 core, coated with VEPEP-9a; NANO-9F/C4: VEPEP-9f/C4 core, coated with VEPEP-9f; NANO-9A-PEG/C4: VEPEP-9a/C4 core, coated with PEG-VEPEP-9a; C4S: VEPEP-9 NANOPEP particles with scrambled C4 peptide.

VEPEP-9 Mediated Delivery of Small Hydrophobic Molecules in Different Cell Lines VEPEP-9 peptides (VEPEP-9a, b, d, f variants) have been used for the delivery of different small fluorescent hydrophobic and charged molecules as well as doxorubicin/porphyrin/taxol on different cell lines including primary cell lines and challenging cell lines. VEPEP-9 peptides form stable particles with small aromatic molecules including doxorubicin or fluorescent dyes (FIG. 10). The dissociation constant for small hydrophobic molecules ranges between 0.01 to 2 µM, depending on the nature of the dyes and of the molecule.

Effect of VEPEP-9 mediated delivery of doxorubicin and porphyrin or taxol have been investigated on cancer cell viability, the different SMHs were complexed with VEPEP-9 peptide at a molar ratio of 1/20. The impact of carrier peptides to improve cellular uptake of small molecule drugs was estimated by following inhibition of proliferation of cancer cells. Dose-response experiments performed on cultured cells revealed that VEPEP-9 mediated delivery of doxorubicin, porphyrin and taxol induced a biological response associated to cell cycle arrest and decrease in viability of MCF7, SCK-3-HEK2 cancer cells (FIG. 10).

$IC_{50}$ are reported in Table 6. Comparison of VEPEP-9 mediated drug delivery with the response obtained with free drug, demonstrated that Doxo, porphyrin and taxol are between 25 to 50-fold more efficient when complexed with VEPEP-9.

TABLE 6

| Drug | VEPEP-9a IC50 (µM) | VEPEP-9b IC50 (µM) | VEPEP-9d IC50 (µM) | VEPEP-9f IC50 (µM) | Free drug IC50 (µM) |
|---|---|---|---|---|---|
| Doxo (SKB3) | 0.2 | 0.3 | 0.4 | 0.6 | 10 |
| Doxo (MCF7) | 0.1 | 0.2 | 0.17 | 0.7 | 9 |
| Porphyrin (MCF7) | 0.8 | 1.4 | 0.54 | 1.2 | 25 |
| Porphyrin (SKB3) | 1.2 | 0.9 | 0.87 | 1.4 | 17 |
| Taxol (MCF7) | 0.8 | 0.12 | 0.5 | 0.8 | 7 |
| Taxol (SKB3) | 0.7 | 0.65 | 0.7 | 0.9 | 10 |

Example 4

NANOPEP-9 Formulations and Applications for In Vivo Delivery

NANOPEP particles contain a "peptide-core" or "core shell" corresponding to the association of either VEPEP-9 peptide or any other peptide forming non covalent complexes with its respective cargo, that is surrounded by additional VEPEP-9 "peripheral" peptides stabilizing the particle and favouring cell membrane association. The efficiency of NANOPEP is mainly controlled by the size and the charge of the particles, which should be ranging between 100-200 nm and $^+5$-$^+20$ Volts, respectively. Several combinations can be used for the "core" and peripheral VEPEP-9 can be functionalized or not. The choice of the peptides in the "core" is dependent on the nature of the cargoes and can be either VEPEP-9, one of the VEPEP-family peptides (VEPEP-6, VEPEP-3, . . . ), CADY (Crombez et al, 2009a [10]), MPG (Crombez et al, 2009b [1]) or PEP-1 (Chariot: Morris et al, 2001 [8]).

The NANOPEP particles are formed in a two step process (FIG. 11): first the "core" at molar ratio of 1/5 or 1/10, and then the "peripheral" at molar ratio of 1/20 up to 1/80. The multilayer organization of the particle allows their oriented functionalization, which is chosen depending on the nature of the cellular target/tissue and administration mode.

A three step protocol (FIG. 11) has been established when particle functionalization takes place via the nitrilotriacetic acid (NTA) linked to the VEPEP-9. NTA-group is well known as being able to chelate metal and to strongly interact with histidine tagged protein. Coating of the particles with NTA-functionalized VEPEP-9 allows the attachment any protein harboring a histidine tag to the particle. That strategy offers the major advantage of having a common 2 layers particles "NANOPEPHIS" that can be associated to any His-tagged protein. The NANOPEPHIS strategy has been used to coat the particles with specific antibody targeting cell surface antigen (EGF, HER-2 or MUC1) or nanobody selected by phage display against specific cell line for targeted-delivery of peptide. NANOPEPHIS-9 strategy can be universally used to any peptides and proteins harbouring a Histidine cluster in their sequence.

Example 5

In Vivo Application of NANOPEP-9 Strategy

NANOPEP-9 strategy has been used for in vivo delivery and targeting of different cargos and different peptide-based nanoparticles. Different examples of NANOPEP-9 applications are reported thereafter for peptide (5.1), siRNA (5.2), PNA (5.3) and small molecule (5.4).

Example 5.1

NANOPEP-9 Mediated Short Peptide In Vivo Targeted Delivery after Systemic Intravenous or Topical Injections NANOPEP-9/Peptide Formulations for In Vivo Administration The therapeutic potential of the NANOPEP-9 technology has been validated in vivo with peptides targeting CDK2/CYCLIN A/E, an essential protein kinase required for the control of cell cycle progression in G1 and G2 and established therapeutic target in several cancers. The potency of this technology has been validated in vivo with peptides targeting interaction between protein kinase and its cyclin regulators, required for entry and progression through mitosis. Peptide C4 combined with NANOPEP (VEPEP-9a or VEPEP-9f) prevents lung and prostate tumour growth in xenografted mouse models, upon injection every three days of NANOPEP-9/C4 at 1 mg/kg (FIG. 12). The "core" shell of the particles was formed using VEVEP-9a or VEPEP-9f peptides at a molar ratio of 20/1 with C4 peptides. VEPEP-9 peptides were solubilised in water and stock solution of peptide was sonicated for 10 min. in a water bath before complex formation. Then VEPEP-9/peptide complexes were formed by adding C4 peptide into the peptide solution and incubating at 37° C. for 20-30 minutes to allow the carrier peptide/peptide complexes to form. Then the particles were coated with either VEPEP-9a (NANOPEP-9a) peptide or VEPEP-9f (NANOPEP-9f) peptides.

The stability of drug-carrier formulations in vivo and in the blood circulation is a major issue for systemic administration of therapeutics. In order to improve the bioavailability and stability of the NANOPEP-9/peptide particles, they were coated with PEG-VEPEP-9, thereby rendering them more suitable for systemic administration. The surface layer of NANOPEP-9 particles was functionalized with a PEG-moiety at the N-terminus of VEPEP-9 (PEG-VEPEP-9a), through activation of the N-terminal beta alanine amino group. Pegylated-NANOPEP-9a/C4 particles were obtained stepwise by complexing VEPEP-9a molecules with C4 at a molar ratio of 15/1, followed by coating of particles with a second layer of PEG-VEPEP-9a at ratio 1/10 and then incubating for 20 minutes at 37° C. for obtaining stable complexes (see FIG. 11). Particles can be lyophilized for long time storage; in that case, 5 to 20% of glucose or manitol are added to the particle solution before lyophilization to stabilize the particles during the process. Before administration, the particles have been diluted in physiological conditions, in the presence of 0.9% NaCl and 5 to 20% glucose or manitol. Following that manufacturing process, more than 95% of the C4 peptides are trapped in the nanoparticles, and the particles are stable for more than 9 months at 4° C., 20° C., −4° C. and −80° C.

NANOPEP-9/C4 Delivery Upon Topical and Systemic Injection

The potential of NANOPEP-9 to deliver C4 peptide in vivo was evaluated on both human prostate carcinoma cell PC3 and SKB3-HEK2 xenografted mice (FIG. 12). The effect of local intratumoral and systemic intravenous administration of NANOPEP-9a/C4 or NANOPEP-9f/C2 particles (molar ratio 20/1) on the growth of established subcutaneous tumours was evaluated. At day 50, tumor sizes in the control cohort, injected with PBS had increased by about 4.0 fold. Upon local intratumoral treatment, every four days, reductions of tumor growth by about 70% and 65% were observed using 100 μg (0.5 mg/kg) of C4/NANOPEP-9a and C4/NANOPEP-9f, for PC3 and SKB3-HEK2, respectively. In both cases, tumour growth was completely prevented with 200 μg (1 mg/kg) C4/NANOPEP-9a and C4/NANOPEP-9f (FIG. 12).

Upon systemic intravenous administration, reductions of tumor growth by 45% and 30% were observed using 200 μg (1 mg/kg) of C4/NANOPEP-9a and C'/NANOPEP-9f, respectively. In contrast, when C4 peptide is associated to functionalized-NANOPEP-9a particles, its potency to inhibit tumour growth after systemic intravenous administration is significantly improved. 100 μg (0.5 mg/kg) of C4 peptide complexed with PEG-NANOPEP-9f at a 1/20 ratio were injected intravenously every three days into mice bearing PC3 or SKB3-HEK2 xenografted tumors and a significant reduction in tumor size of 90% was observed at day 50 (FIG. 12), which is 10 to 20-fold more potent than the non functionalized-NANOPEP-9 nanoparticle, suggesting that PEG-increases the biodistribution of peptide in the tumour by maintaining peptide in the plasma and by stabilizing the NANOPEP-9 particle.

In both cases, inhibition of tumour growth was C4 sequence-specific as scrambled peptides C4S or complexed with NANOPEP-9a or NANOPEP-9f and injected into mice at 2 mg/kg was unable to inhibit tumour growth. The results demonstrated that NANOPEP-9 particles are less efficient via systemic injection, which is probably due to lower stability in the blood of the particle (see below).

Example 5.2

Figure 13:
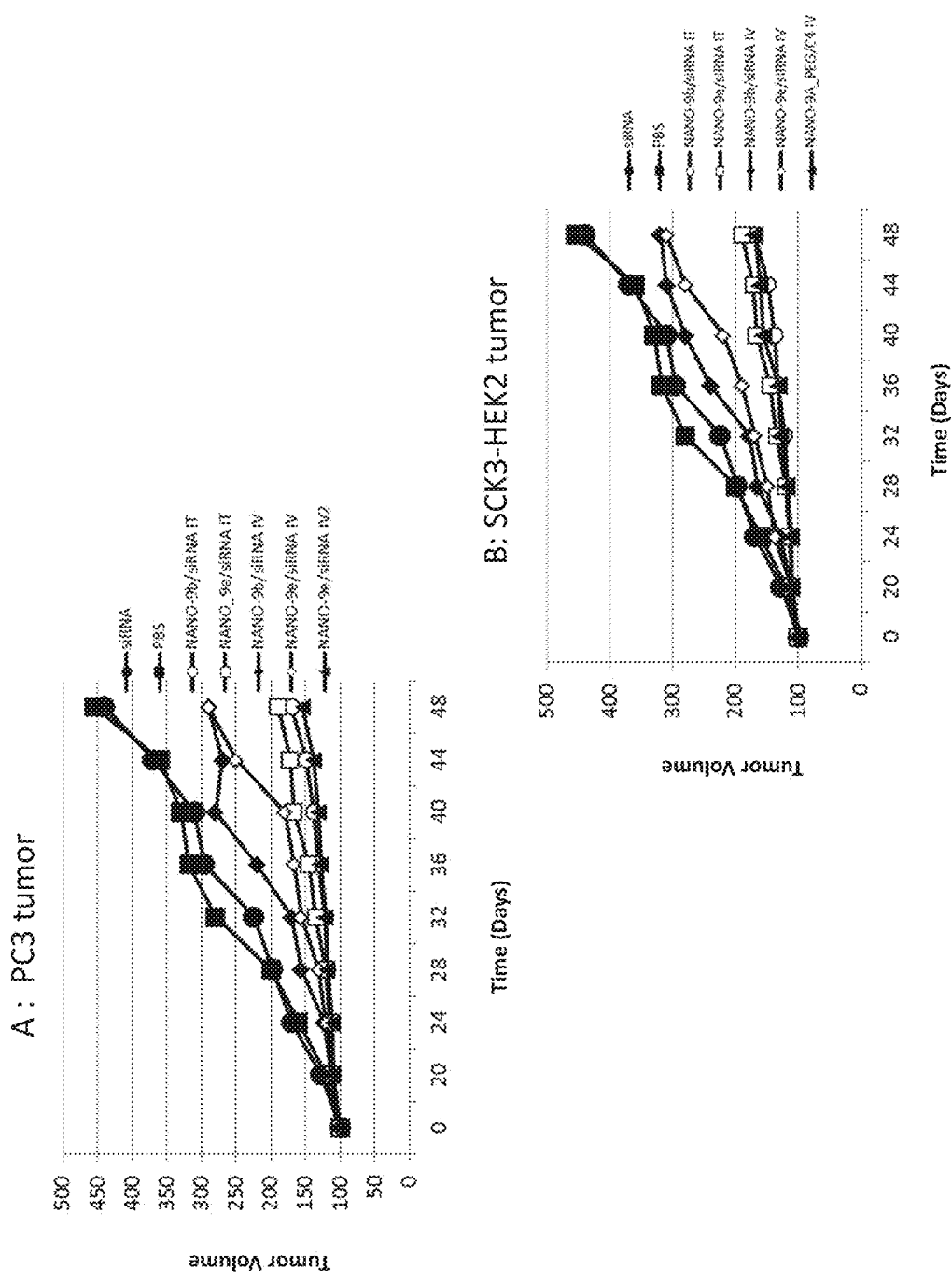
FIGS. 13A and 13B show reduction of tumor growth by intratumoral (IT) or intravenous (IV) administration of NANOPEP particles containing siRNA targeting Cyclin B1 in PC3 (13A) or SCK3-HEK2 (13B) xenograft mice. NANO-9b/siRNA: VEPEP-9b/siRNA core, coated with VEPEP-9b; NANO-9e/siRNA: VEPEP-9e/siRNA core, coated with VEPEP-9e; NANO-9A-PEG/C4: VEPEP-9a/C4 core, coated with PEG-VEPEP-9a; siRNA: control siRNA targeting Cyclin B3.

NANOPEP-9 Mediated siRNA In Viva Targeted Delivery after Systemic Intravenous or Topical Injections Combining cyclin B1 siRNA with NANOPEP-9 prevents lung, ovarian and prostate tumour growth in xenografted mouse models, upon injection every three days of NANO-PEP-9/siRNA complexes (FIG. 13).

Athymic female nude mice (6-8 weeks of age) were subcutaneously inoculated into the flank with 1×10 PC3 (prostate cancer), A549 (lung cancer) or SCK-3-HEK2 (ovarian cancer) cells in 100 µl PBS. Two to three weeks after tumour implant, when tumour size reached about 100 mm$^3$, animals were treated by intratumoral or intravenous injection, every 3 days, with a solution of 0.1 ml of either free Cyc-B1 siRNA (50 or 100 µg), control siRNA Cyc-B3 or Cyc-B1 siRNA (5, 10 µg) complexed with NANOPEP-9b or NANOPEP-9e particles. The "core" shell of the particles was formed using VEVEP-9b or VEPEP-9e peptide at a molar ratio of 20/1 with a siRNA targeting cycline B1. siRNA stock solutions are in 50 mM Iris, 0.5 mM EDTA buffer or in RNase free water. VEPEP-9 peptides were solubilised in water and stock solution of peptide was sonicated for 10 min in a water bath before complex formation. Then VEPEP-9/siRNA complexes were formed by adding siRNA into the peptide solution and incubating at 37° C. for 20-30 minutes to allow the carrier peptide/siRNA complexes to form. NANOPEP-9 particles contain a VEPEP-9/siRNA "core shell" surrounded by additional VEPEP-9 at a 1/20 molar ratio.

Tumour diameter was measured in two directions at regular intervals using a digital calliper and tumour volume was calculated as length×width×height×0.52. Curves show the mean value of tumour size in a cohort of six animals and neither animal death nor any sign of toxicity were observed. Experiments were performed according to national regulations and approved by the local animal experimentation ethical committee. The statistical significance of the results was calculated by Student's t test and p<0.05 considered to be statistically significant. The stock solutions of particles were done in water and stable for at least three weeks at 4° C. Particles can be lyophilized for long time storage; in that case, 5 to 20% of glucose is added to the particle solution before lyophilization to stabilize the particles during the process. Before administration the particles were diluted in physiological conditions, in the presence of 0.9% NaCl and 5 to 20% manitol.

NANOPEP-9 Cyclin B1 siRNA Delivery Upon Topical Injection

The potential of NANOPEP-9b or NANOPEP-9e to deliver cyclin B1 siRNA in vivo was evaluated on PC3. A549, or SCK-3-HEK2-xenografted mice (FIG. 13). The effect of local intratumoral administration of NANOPEP-9/siRNA particles (molar ratio 20/1) on the growth of established subcutaneous tumours was evaluated. At day 50, tumor sizes in the control cohort, injected with PBS increased by about 3 to 5 fold. Reductions of tumor growth by 80% (PC3 and A549) and by 65% (SCK-3-HEK2), were observed using 1 µg of cyclin B1 siRNA in NANOPEP-9/siRNA and in all the cases, tumour growth was completely prevented with 5 µg (0.25 mg/kg) of cyclin B1 siRNA in NANOPEP-9/siRNA (FIG. 13). At day 48, it was validated that the Cyc-B1 siRNA mediated inhibition of tumour growth was directly associated with a decrease in the level of cyclin B1 mRNA. As a control, administration of 100 µg (intratumoral or intravenous) naked siRNA or NANOPEP-9 carrier alone had no significant effect on tumour growth. Moreover, inhibition of tumour growth was siRNA sequence-specific as a cyclin B1 siRNA harbouring two mutations (Cyc-B3) complexed with NANOPEP-9e and injected into mice at 0.5 mg/kg was unable to inhibit tumour growth.

NANOPEP-9 Cyclin B1 siRNA Delivery Upon Systemic Injection

NANOPEP-9b and NANOPEP-9e particles were used for systemic intravenous administration. Five micrograms (0.25 mg/kg) and 10 µg (0.5 mg/kg) of Cyc B1 siRNA in NANOPEP-9b and NANOPEP-9e particles were injected intravenously every three days into mice bearing xenografted tumors. A significant reduction in PC3 tumor size was observed at day 50, with 65% and 90% inhibition with 5 µg and 10 µg of siRNA, respectively (FIG. 13). A significant reduction in HT29 tumor size was observed at day 50, with 35% and 70% inhibition with 5 µg and 10 µg of siRNA, respectively (Figure xx). These results together with the lack of anti-tumoral activity of the NANOPEP-9/mismatch siRNA (10 µg) or of NANOPEP-9 carrier alone, underscores the robustness and specificity of the biological response associated with systemic delivery of cyclin B1 siRNA Example 5.3

NANOPEP-9 Mediated Anti Cyclin B1 PNA Antisens Delivery Upon Systemic Injection

Figure 14:
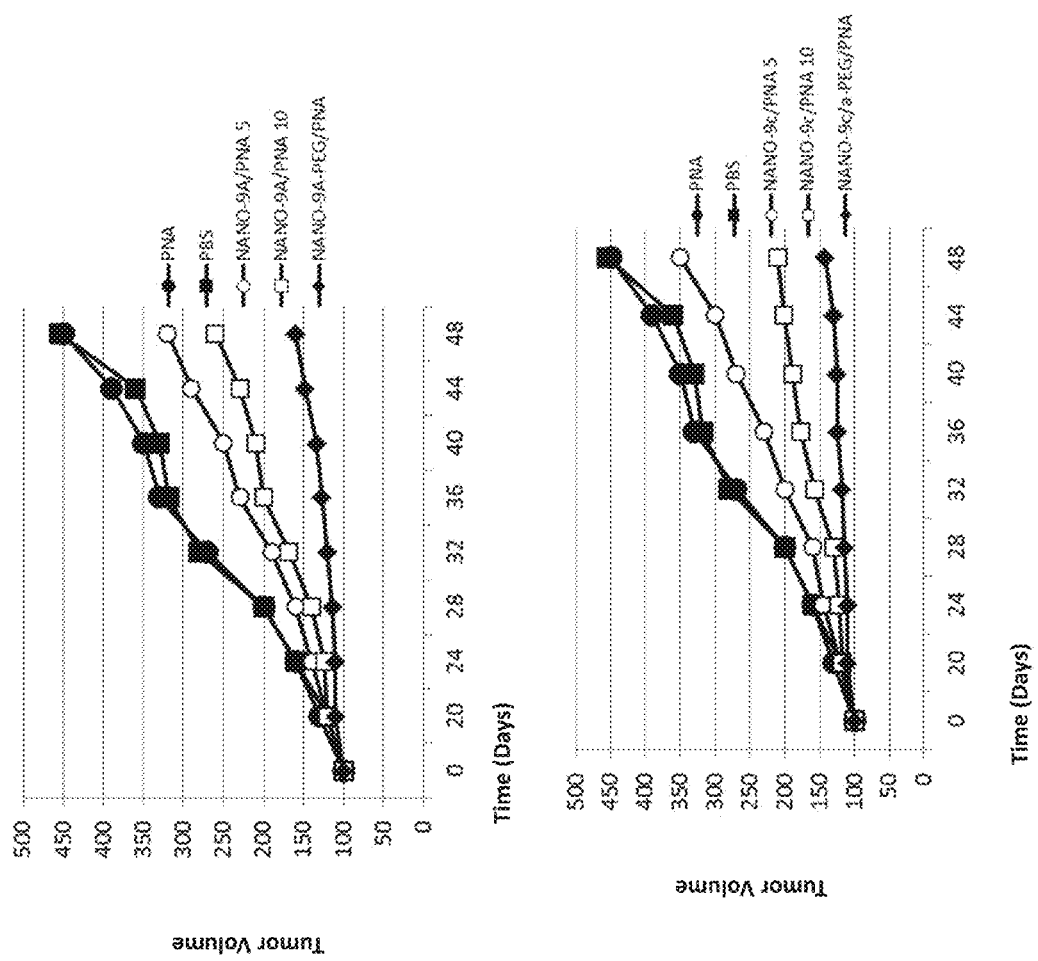

NANOPEP-9a and NANOPEP-9c were used for the delivery of antisense PNA targeting cyclin B1 antisense in vivo. NANOPEP-9a/PNA, NANOPEP-9c/PNA and NANOPEP-9a/PNA particles coated with PEG-VEPEP-9a were evaluated directly on the potency to inhibit tumour growth. The particles were used for systemic intravenous administration into SKB3-HEK2 xenografted tumor mouse model. The surface layer of NANOPEP-9a particles was functionalized with a PEG-moiety at the N-terminus of VEPEP-9a (PEG-VEPEP-9a), through activation of the N-terminal beta-alanine amino group. Pegylated-NANO-PEP-9a/PNA particles were obtained stepwise by complexing VEPEP-9a molecules with PNA at a molar ratio of 10/1, followed by coating of particles with a second layer of PEG-VEPEP-9a at ratio 1/10. 10 µg of PNA complexed with NANOPEP-9a, NANOPEP-9e and PEG-NANOPEP-9a at a 1/30 ratio were injected intravenously every three days into mice bearing SKB3-HEK2 xenografted tumor. As reported in FIG. 14, at day 50, reductions of tumor growth by 35 and 42% were obtained with 10 µg of PNA complexed with NANOPEP-9a and NANOPEP-9e, respectively. A significant reduction in tumor size of 78% was observed with 10 µg of PNA complexed with PEG-NANOPEP-9a, at day 50 (FIG. 14). Inhibition of tumour growth was PNA cyclin B1 sequence-specific as 50 µg scrambled PNA complexed with NANOPEP-9a and injected into mice was unable to inhibit tumour growth. These results show that VEPEP-9a and VEPEP-9e constitute great carriers for in vivo delivery of PNA and that PEG-increases the biodistribution of PNA in the tumour by improving the stability of the NANOPEP-9 particle.

Example 5.4

NANOPEP-9 Mediated Doxomycin In Vivo Delivery Upon Systemic Injection

Figure 15:
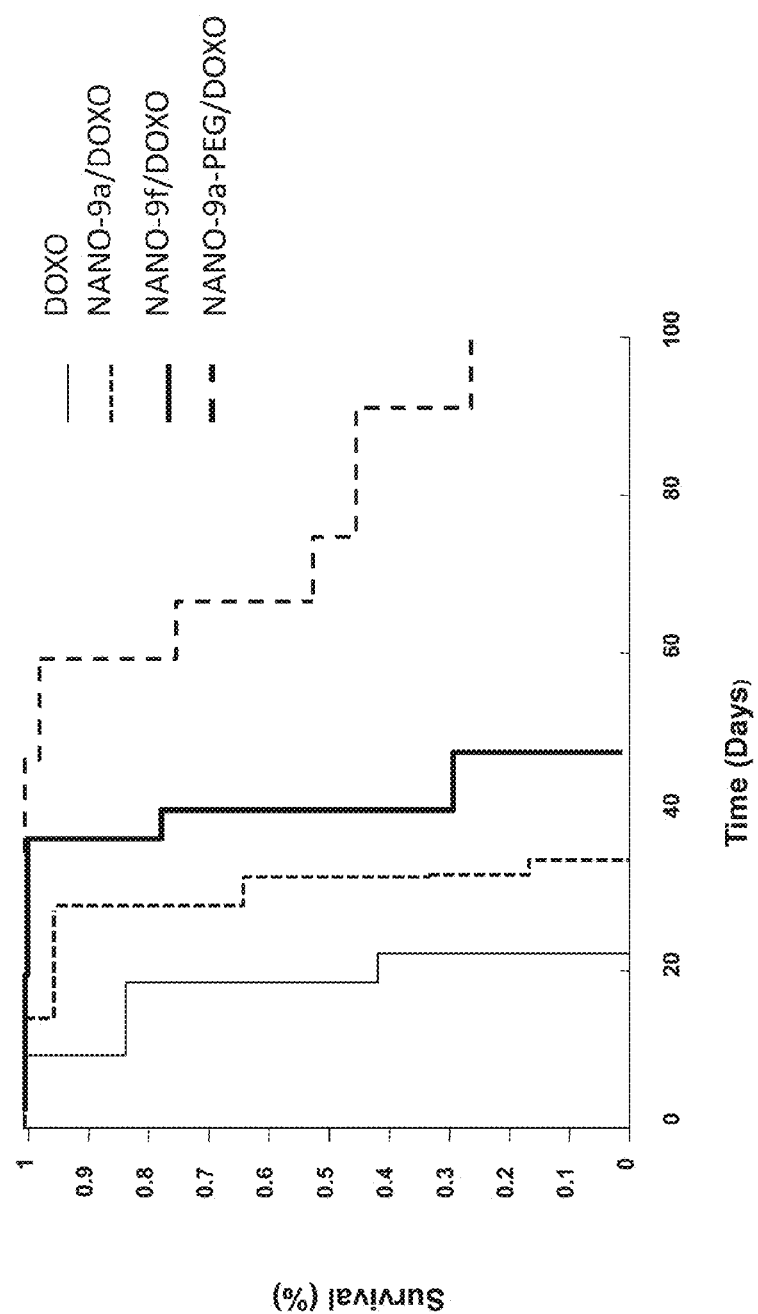
FIG. 15 shows survival of SKB3-HEK2 xenograft mice following administration of NANOPEP particles containing doxorubicin (DOXO). NANO-9a/DOXO: VEPEP-9a/DOXO core, coated with VEPEP-9a; NANO-9F/DOXO: VEPEP-9f/DOXO core, coated with VEPEP-9f; NANO-9a-PEG/DOXO: VEPEP-9a/DOXO core, coated with PEG-EPEP-9a; DOXO: DOXO alone.

NANOPEP-9 peptides (VEPEP-9a, b, d, f variants) have been used for the delivery of doxorubicin in vivo. The potential of NANOPEP-9 to deliver doxorubicin in vivo was evaluated on SKB3-HEK2 xenografted mice. Doxorubicin was complexed with VEPEP-9 peptide at a molar ratio of 1/20 with NANOPEP-9a, NANOPEP-9f and NANOPEP-9a-PEG. The treatment was started 10 days after tumor inoculation and with 2 mg/kg and 10 mg/Kg doses of drug and injected every 4 days by systemic Intravenous administration and mice were monitored for survival (FIG. 15). The results demonstrate a survival rate of 10 days in the absence of any drug, of 16 days with free Doxo (20 mg/Kg), of 32 and 45 days with 10 mg/kg complexed with NANOPEP-9a or NANOPEP-f, respectively. When particles are coated with PEG-NANOPEP-9a, more than 45% of the mice were still surviving after 50 days, suggesting that PEGylation dramatically improves the bioavailability of the particles.

Example 5.5

NANOPEP-9 Mediated In Vivo Delivery of Cargo Via Different Administration Routes NANOPEP-9 based particles have been evaluated using different administration routes including systemic intravenous, intrarectal, intranasal and transdermal administrations.

Figure 16:
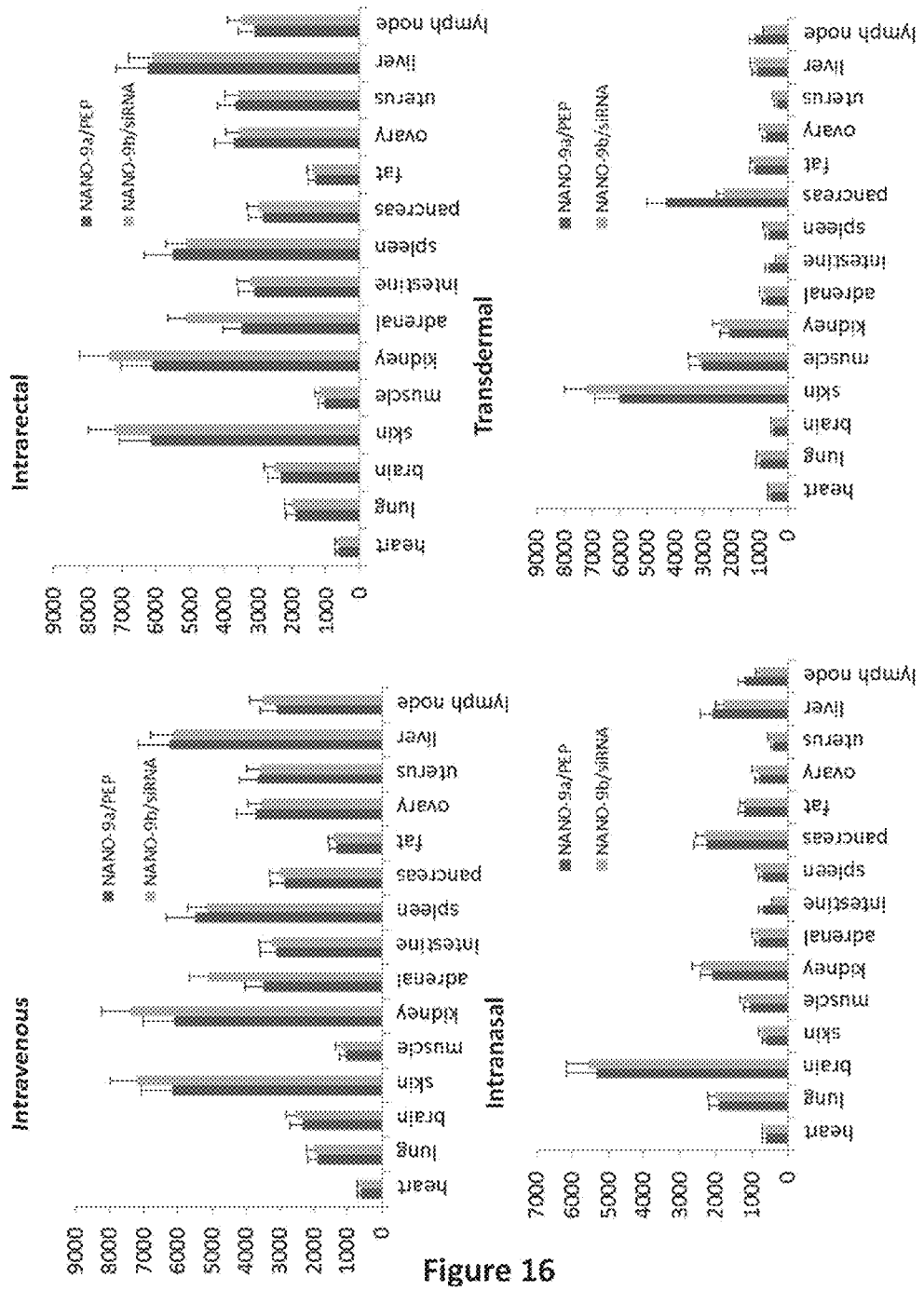
FIG. 16 shows in vivo biodistribution of fluorescently labeled peptide (PEP) or siRNA delivered by intravenous, intrarectal, intranasal or transdermal administration of VEPEP-9 NANOPEP particles (as determined by live fluorescence animal imaging). NANO-9a/PEP: VEPEP-9a/peptide core, coated with VEPEP-9a; NANO-9b/siRNA: VEPEP-9b/siRNA core, coated with VEPEP-9b.

A fluorescently labelled peptide or siRNA with Alexa 700 was complexed into NANOPEP-9a or NANOPEP-9b particles. Biodistribution of the fluorescently labelled peptide or siRNA was evaluated in vivo on Balb6 Mouse, 5 hr after a single administration of 10 µg peptide or siRNA in NANOPEP-9 particles. Intravenous and intrarectal administrations of the NANOPEP-9/peptide or NANOPEP-9/siRNA complex allowed the delivery of the cargoes in most of the analyzed tissues, with a significant delivery in the lung and muscle (FIG. 16). Intranasal and intratracheal administration allowed the delivery of peptide and siRNA, mainly in the brain, lung, liver, pancreas and kidney. Finally, transdermal administration is limited to the delivery of the peptide and siRNA into and through the skin and muscles, and partially in the liver but not in the other tissues (FIG. 16).

REFERENCES

[1] D J. Glover, H J. Lipps, D A. Jans, Towards safe, non-viral therapeutic gene expression in humans. Nat. Rev, Genet. 6 (2005) 299-310

[2] K A. Whitehead, R. Langer, D G. Anderson, Knocking down barriers: advances in siRNA delivery. Nat Rev Drug Discov. 8 (2009) 129-138.

[3] Ü Langel, Handbook of Cell-Penetrating Peptides: (Eds.: U. Langel) CRC Taylor & Francis, Boca Raton (2007).

[4] F. Heitz, M C. Morris, G. Divita, Twenty years of cell-penetrating peptides: from molecular mechanisms to therapeutics; British Journal of Pharmacology 157 (2009) 195-206.

[5] S. Deshayes, M C Morris, F. Heitz, G. Divita. Delivery of proteins and nucleic acids using a non-covalent peptide-based strategy. Adv Drug Deliv Rev. 60 (2008) 537-547.

[6] S. Deshayes, M C. Morris, G. Divita, F. Heitz Cell-penetrating peptides: tools for intracellular delivery of therapeutics, Cell Mol Life Sci. 62 (2005) 1839-1849.

[7] M C. Morris, P. Vidal, L. Chaloin, F. Heitz, G Divita A new peptide vector for efficient delivery of oligonucleotides into mammalian cells, Nucleic Acids Res. 25 (1997) 2730-2736.

[8] M C. Morris, J. Depollier, J. Mery, F. Heitz, G. Divita A peptide carrier for the delivery of biologically active proteins into mammalian cells, Nat. Biotechnol. 19 (2001) 1173-1176.

[9] Mery J, Brugidou J, Derancourt J. Disulfide bond as peptide-resin linkage in Boe-Bzl SPPS, for potential biochemical applications. Pept Res. 1992 July-August; 5(4):233-40.

[10] L. Crombez, M. C. Morris, S. Dufort, G. Aldrian-HeiTada, Q. Nguyen, G. Mc Master. J. L. Coll, F. Heitz, G. Divita, Targeting cyclin B1 through peptide-based delivery of siRNA prevents tumour growth, Nucleic Acids Res. 37 (2009) 4559-4569.

[11] L. Crombez, G. Aldrian-Herrada, K. Konate, Q. N. Nguyen, G. K. McMaster, R. Brasseur, F. Heitz. G. Divita, A new potent secondary amphipathic cell penetrating peptide for siRNA delivery into mammalian cells, Mol. Ther. 17 (2009) 95-103.

[12] Verdins, G. L. and Hilinski, G. J. (2012), Stapled peptides or intracellular drug targets. Methods in Enzymology, vol 503, p 3-33.

The invention claimed is:

1. A cell-penetrating peptide characterized in that it comprises an amino acid sequence: $X_1X_2X_3WWX_4X_5WAX_6X_3X_7X_8X_9X_{10}X_{11}X_{12}WX_{13}R$ (SEQ ID No: 10), wherein $X_1$ is beta-A or S, $X_2$ is L or none, $X_3$ is R or none, $X_4$ is L, R or G, $X_5$ is R, W or S, $X_6$ is S, P or T, $X_7$ is W or P, $X_8$ is F, A or R, $X_9$ is S, L, P or R, $X_{10}$ is R or S, $X_{11}$ is W or none, $X_{12}$ is A, R or none and $X_{13}$ is W or F, and wherein if $X_3$ is none, then $X_2$, $X_{11}$ and $X_{12}$ are none as well.

2. The cell-penetrating peptide of claim 1, characterized in that it comprises an amino acid sequence $X_1X_2RWWLRWAX_6RWX_8X_9X_{10}WX_{12}WX_{13}R$ (SEQ ID No: 11), wherein $X_1$ is beta-A or S, $X_2$ is L or none, $X_6$ is S or P, $X_8$ is F or A, $X_9$ is S, L or P, $X_{10}$ is R or S, $X_{12}$ is A or R, and $X_{13}$ is W or F.

3. The cell-penetrating peptide of claim 2, wherein the amino acid sequence is selected from the group consisting of:

$X_1$LRWWLRWASRWFSRWAWWR, (SEQ ID No: 1)

$X_1$LRWWLRWASRWASRWAWFR, (SEQ ID No: 2)

$X_1$RWWLRWASRWALSWRWWR, (SEQ ID No: 3)

$X_1$RWWLRWASRWFLSWRWWR, (SEQ ID No: 4)

$X_1$RWWLRWAPRWFPSWRWWR, (SEQ ID No: 5)
and $X_1$RWWLRWASRWAPSWRWWR, (SEQ ID No: 6)

wherein $X_1$ is beta-A or S.

4. The cell-penetrating peptide of claim 1, characterized in that it comprises an amino acid sequence $X_1WWX_4X_5WAX_6X_7X_8RX_{10}WWR$ (SEQ ID No: 12), wherein $X_1$ is beta-A or S, $X_4$ is R or G, $X_5$ is W or S, $X_6$ is S, T or P, $X_7$ is W or P, $X_8$ is A or R, and $X_{10}$ is S or R.

5. The cell-penetrating peptide of claim 4, wherein the amino acid sequence is selected from the group consisting of:

$X_1$WWRWWASWARSWWR, (SEQ ID No: 7)

$X_1$WWGSWATPRRRWWR, (SEQ ID No: 8)
and $X_1$WWRWWAPWARSWWR, (SEQ ID No: 9)

wherein $X_1$ is beta-A or S.

6. The cell-penetrating peptide of claim 1, further comprising, covalently linked to the N-terminal end of the amino acid sequence, one or several chemical entities selected from the group consisting of an acetyl, a fatty acid, a cholesterol, a poly-ethylene glycol, a nuclear localization signal, a nuclear export signal, an antibody, a polysaccharide and a targeting molecule.

7. The cell-penetrating peptide of claim 1, further comprising, covalently linked to the C-terminal end of said amino acid sequence, one or several groups selected from the group consisting of a cysteamide, a cysteine, a thiol, an amide, an optionally substituted nitrilotriacetic acid, a carboxyl, a linear or branched optionally substituted $C_1$-$C_6$ alkyl, a primary or secondary amine, a lipid, a phospholipid, a fatty acid, a cholesterol, a poly-ethylene glycol, a nuclear localization signal, a nuclear export signal, an antibody, a polysaccharide and a targeting molecule.

8. A complex comprising a cell-penetrating peptide according to claim 1 and a cargo selected amongst peptides, proteins, peptide analogs, oligonucleotides, PNAs and small hydrophobic molecules.

9. The complex of claim 8, wherein said cargo is a molecule of at most 1.5 kDa.

10. The complex of claim 8, wherein said cargo is an anticancer or an anti-viral drug.

11. The complex of claim 8, wherein said cargo is selected from the group consisting of siRNA, a mix of siRNAs selected to silence a target mRNA, miRNA, a mix of miRNAs, oligodeoxynucleotides, amino acids, di- or tri-peptides, daunomycin, Paclitaxel, doxorubicin, AZT, porphyrin, fluorescently labelled nucleosides or nucleotides, hydrophobic maghemite and fluorescent dyes.

12. The complex of claim 8, wherein the size of the complex is between 50 and 300 nm.

13. A nanoparticle comprising a complex according to claim 8, coated by a layer of peripheral cell-penetrating peptides, wherein said peripheral cell-penetrating peptides have a peptide sequence different from SEQ ID No: 10, SEQ ID No: 11 and SEQ ID No: 12.

14. A nanoparticle comprising a core which comprises a cargo complexed to a first entity selected from the group consisting of cell-penetrating peptides, liposomes, polycationic structures and carbon nanoparticles, wherein said core is coated by peripheral cell-penetrating peptides, and wherein the peripheral cell-penetrating peptides have the peptide sequence of a cell-penetrating peptide according to claim 1.

15. The nanoparticle of claim 14, wherein said first entity is a cell-penetrating peptide selected from the group consisting of VEPEP-6a (SEQ ID No: 33), VEPEP-6b (SEQ ID No: 34), VEPEP-6c (SEQ ID No: 35), VEPEP-6d (SEQ ID No: 36), VEPEP-6e (SEQ ID No: 37), VEPEP-6f (SEQ ID No: 38), ST-VEPEP-6a (SEQ ID No: 41), ST-VEPEP-6aa (SEQ ID No: 42), ST-VEPEP-6ab (SEQ ID No: 43), ST-VEPEP-6ad (SEQ ID No: 44), ST-VEPEP-6b (SEQ ID No: 45), ST-VEPEP-6ba (SEQ ID No: 46), ST-VEPEP-6bb (SEQ ID No: 47), ST-VEPEP-6bd (SEQ ID No: 48), ST-VEPEP-6c (SEQ ID No: 49), VEPEP-3a (SEQ ID No: 25), VEPEP-3b (SEQ ID No: 26), VEPEP-3c (SEQ ID No: 27), VEPEP-3d (SEQ ID No: 28), VEPEP-3e (SEQ ID No: 29), VEPEP-3f (SEQ ID No: 30), VEPEP-3g (SEQ ID No: 31), VEPEP-3h (SEQ ID No: 32), VEPEP-3bstapl (SEQ ID No: 39), VEPEP-3estapl (SEQ ID No: 40), CADY, MPG, PEP-1, PPTG1, and poly Arginine.

16. The nanoparticle of claim 14, wherein the size of the nanoparticle is between 20 and 300 nm.

17. The nanoparticle of claim 14, wherein the peripheral cell-penetrating peptides comprise a poly-ethylene glycol group covalently linked to their N-terminus, and/or a cysteamide group covalently linked to their C-terminus.

18. The nanoparticle of claim 14, wherein at least some of the peripheral cell-penetrating peptides are bound to a targeting molecule.

19. The nanoparticle of claim 14, for use as a medicament.

20. The nanoparticle of claim 14, for use as a marker or an imaging agent.

21. A therapeutic, cosmetic or diagnostic composition comprising a nanoparticle according to claim 14.

22. The composition of claim 21, which is formulated for intravenous, intratumoral, topical, intrarectal, intranasal, transdermal, or intradermal administration, or for administration via a mouth spray, or for administration as a subcutaneous implant for slow release of a drug.

23. A method for delivering a molecule into a cell in vitro, comprising a step of putting said cell into contact with a nanoparticle according to claim 14, wherein the cargo of the nanoparticle is said molecule.

* * * * *

SEQUENCE LISTING

```
<160> NUMBER OF SEQ ID NOS: 54

<210> SEQ ID NO 1
<211> LENGTH: 20
<212> TYPE: PRT
<213> ORGANISM: Artificial
<220> FEATURE:
<223> OTHER INFORMATION: VEPEP9a1
<220> FEATURE:
<221> NAME/KEY: MISC_FEATURE
<222> LOCATION: (1)..(1)
<223> OTHER INFORMATION: X = beta-A or S

<400> SEQUENCE: 1

Xaa Leu Arg Trp Trp Leu Arg Trp Ala Ser Arg Trp Phe Ser Arg Trp
```

```
1               5                   10                  15
Ala Trp Trp Arg
            20

<210> SEQ ID NO 2
<211> LENGTH: 20
<212> TYPE: PRT
<213> ORGANISM: Artificial
<220> FEATURE:
<223> OTHER INFORMATION: VEPEP9a2
<220> FEATURE:
<221> NAME/KEY: MISC_FEATURE
<222> LOCATION: (1)..(1)
<223> OTHER INFORMATION: X = beta-A or S

<400> SEQUENCE: 2

Xaa Leu Arg Trp Trp Leu Arg Trp Ala Ser Arg Trp Ala Ser Arg Trp
1               5                   10                  15

Ala Trp Phe Arg
            20

<210> SEQ ID NO 3
<211> LENGTH: 19
<212> TYPE: PRT
<213> ORGANISM: Artificial
<220> FEATURE:
<223> OTHER INFORMATION: VEPEP9b1
<220> FEATURE:
<221> NAME/KEY: MISC_FEATURE
<222> LOCATION: (1)..(1)
<223> OTHER INFORMATION: X = beta-A or S

<400> SEQUENCE: 3

Xaa Arg Trp Trp Leu Arg Trp Ala Ser Arg Trp Ala Leu Ser Trp Arg
1               5                   10                  15

Trp Trp Arg

<210> SEQ ID NO 4
<211> LENGTH: 19
<212> TYPE: PRT
<213> ORGANISM: Artificial
<220> FEATURE:
<223> OTHER INFORMATION: VEPEP9b2
<220> FEATURE:
<221> NAME/KEY: MISC_FEATURE
<222> LOCATION: (1)..(1)
<223> OTHER INFORMATION: X = beta-A or S

<400> SEQUENCE: 4

Xaa Arg Trp Trp Leu Arg Trp Ala Ser Arg Trp Phe Leu Ser Trp Arg
1               5                   10                  15

Trp Trp Arg

<210> SEQ ID NO 5
<211> LENGTH: 19
<212> TYPE: PRT
<213> ORGANISM: Artificial
<220> FEATURE:
<223> OTHER INFORMATION: VEPEP9c1
<220> FEATURE:
<221> NAME/KEY: MISC_FEATURE
<222> LOCATION: (1)..(1)
<223> OTHER INFORMATION: X = beta-A or S

<400> SEQUENCE: 5

Xaa Arg Trp Trp Leu Arg Trp Ala Pro Arg Trp Phe Pro Ser Trp Arg
1               5                   10                  15
```

Trp Trp Arg

```
<210> SEQ ID NO 6
<211> LENGTH: 19
<212> TYPE: PRT
<213> ORGANISM: Artificial
<220> FEATURE:
<223> OTHER INFORMATION: VEPEP9c2
<220> FEATURE:
<221> NAME/KEY: MISC_FEATURE
<222> LOCATION: (1)..(1)
<223> OTHER INFORMATION: X = beta-A or S

<400> SEQUENCE: 6
```

Xaa Arg Trp Trp Leu Arg Trp Ala Ser Arg Trp Ala Pro Ser Trp Arg
1               5                   10                  15

Trp Trp Arg

```
<210> SEQ ID NO 7
<211> LENGTH: 15
<212> TYPE: PRT
<213> ORGANISM: Artificial
<220> FEATURE:
<223> OTHER INFORMATION: VEPEP9d
<220> FEATURE:
<221> NAME/KEY: MISC_FEATURE
<222> LOCATION: (1)..(1)
<223> OTHER INFORMATION: X = beta-A or S

<400> SEQUENCE: 7
```

Xaa Trp Trp Arg Trp Trp Ala Ser Trp Ala Arg Ser Trp Trp Arg
1               5                   10                  15

```
<210> SEQ ID NO 8
<211> LENGTH: 15
<212> TYPE: PRT
<213> ORGANISM: Artificial
<220> FEATURE:
<223> OTHER INFORMATION: VEPEP9e
<220> FEATURE:
<221> NAME/KEY: MISC_FEATURE
<222> LOCATION: (1)..(1)
<223> OTHER INFORMATION: X = beta-A or S

<400> SEQUENCE: 8
```

Xaa Trp Trp Gly Ser Trp Ala Thr Pro Arg Arg Arg Trp Trp Arg
1               5                   10                  15

```
<210> SEQ ID NO 9
<211> LENGTH: 15
<212> TYPE: PRT
<213> ORGANISM: Artificial
<220> FEATURE:
<223> OTHER INFORMATION: VEPEP9f
<220> FEATURE:
<221> NAME/KEY: MISC_FEATURE
<222> LOCATION: (1)..(1)
<223> OTHER INFORMATION: X = beta-A or S

<400> SEQUENCE: 9
```

Xaa Trp Trp Arg Trp Trp Ala Pro Trp Ala Arg Ser Trp Trp Arg
1               5                   10                  15

```
<210> SEQ ID NO 10
<211> LENGTH: 20
<212> TYPE: PRT
<213> ORGANISM: Artificial
<220> FEATURE:
```

```
<223> OTHER INFORMATION: VEPEP9
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (2)..(2)
<223> OTHER INFORMATION: X = L or none if X in position 3 is R, and
      X = none if X in position 3 is none
<220> FEATURE:
<221> NAME/KEY: MISC_FEATURE
<222> LOCATION: (3)..(3)
<223> OTHER INFORMATION: X = R or none
<220> FEATURE:
<221> NAME/KEY: MISC_FEATURE
<222> LOCATION: (6)..(6)
<223> OTHER INFORMATION: X = L, R or G
<220> FEATURE:
<221> NAME/KEY: MISC_FEATURE
<222> LOCATION: (7)..(7)
<223> OTHER INFORMATION: X = R, W or S
<220> FEATURE:
<221> NAME/KEY: MISC_FEATURE
<222> LOCATION: (10)..(10)
<223> OTHER INFORMATION: X = S, P or T
<220> FEATURE:
<221> NAME/KEY: MISC_FEATURE
<222> LOCATION: (11)..(11)
<223> OTHER INFORMATION: X = R if X in position 3 is R, and X = none
      if X in position 3 is none
<220> FEATURE:
<221> NAME/KEY: MISC_FEATURE
<222> LOCATION: (12)..(12)
<223> OTHER INFORMATION: X = W or P
<220> FEATURE:
<221> NAME/KEY: MISC_FEATURE
<222> LOCATION: (13)..(13)
<223> OTHER INFORMATION: X = F, A or R
<220> FEATURE:
<221> NAME/KEY: MISC_FEATURE
<222> LOCATION: (14)..(14)
<223> OTHER INFORMATION: X = S, L, R or P
<220> FEATURE:
<221> NAME/KEY: MISC_FEATURE
<222> LOCATION: (15)..(15)
<223> OTHER INFORMATION: X = R or S
<220> FEATURE:
<221> NAME/KEY: MISC_FEATURE
<222> LOCATION: (16)..(16)
<223> OTHER INFORMATION: X = W or none if X in position 3 is R, and
      X = none if X in position 3 is none
<220> FEATURE:
<221> NAME/KEY: MISC_FEATURE
<222> LOCATION: (17)..(17)
<223> OTHER INFORMATION: X = A, R, or none if X in position 3 is R,
      and X = none if X in position 3 is none
<220> FEATURE:
<221> NAME/KEY: MISC_FEATURE
<222> LOCATION: (19)..(19)
<223> OTHER INFORMATION: X = W or F

<400> SEQUENCE: 10

Xaa Xaa Xaa Trp Trp Xaa Xaa Trp Ala Xaa Xaa Xaa Xaa Xaa Xaa Xaa
1               5                   10                  15

Xaa Trp Xaa Arg
            20

<210> SEQ ID NO 11
<211> LENGTH: 20
<212> TYPE: PRT
<213> ORGANISM: Artificial
<220> FEATURE:
<223> OTHER INFORMATION: VEPEP9
<220> FEATURE:
<221> NAME/KEY: MISC_FEATURE
```

```
<222> LOCATION: (1)..(1)
<223> OTHER INFORMATION: X = beta-A or S
<220> FEATURE:
<221> NAME/KEY: MISC_FEATURE
<222> LOCATION: (2)..(2)
<223> OTHER INFORMATION: X = L or none
<220> FEATURE:
<221> NAME/KEY: MISC_FEATURE
<222> LOCATION: (10)..(10)
<223> OTHER INFORMATION: X = S or P
<220> FEATURE:
<221> NAME/KEY: MISC_FEATURE
<222> LOCATION: (13)..(13)
<223> OTHER INFORMATION: X = F or A
<220> FEATURE:
<221> NAME/KEY: MISC_FEATURE
<222> LOCATION: (14)..(14)
<223> OTHER INFORMATION: X = S, L or P
<220> FEATURE:
<221> NAME/KEY: MISC_FEATURE
<222> LOCATION: (15)..(15)
<223> OTHER INFORMATION: X = R or S
<220> FEATURE:
<221> NAME/KEY: MISC_FEATURE
<222> LOCATION: (17)..(17)
<223> OTHER INFORMATION: X = A or R
<220> FEATURE:
<221> NAME/KEY: MISC_FEATURE
<222> LOCATION: (19)..(19)
<223> OTHER INFORMATION: X = W or F

<400> SEQUENCE: 11

Xaa Xaa Arg Trp Trp Leu Arg Trp Ala Xaa Arg Trp Xaa Xaa Xaa Trp
1               5                   10                  15

Xaa Trp Xaa Arg
            20

<210> SEQ ID NO 12
<211> LENGTH: 15
<212> TYPE: PRT
<213> ORGANISM: Artificial
<220> FEATURE:
<223> OTHER INFORMATION: VEPEP9
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (4)..(4)
<223> OTHER INFORMATION: X = R or G
<220> FEATURE:
<221> NAME/KEY: MISC_FEATURE
<222> LOCATION: (5)..(5)
<223> OTHER INFORMATION: X = W or S
<220> FEATURE:
<221> NAME/KEY: MISC_FEATURE
<222> LOCATION: (8)..(8)
<223> OTHER INFORMATION: X = S, T or P
<220> FEATURE:
<221> NAME/KEY: MISC_FEATURE
<222> LOCATION: (9)..(9)
<223> OTHER INFORMATION: X = W or P
<220> FEATURE:
<221> NAME/KEY: MISC_FEATURE
<222> LOCATION: (10)..(10)
<223> OTHER INFORMATION: X = A or R
<220> FEATURE:
<221> NAME/KEY: MISC_FEATURE
<222> LOCATION: (12)..(12)
<223> OTHER INFORMATION: X = S or R

<400> SEQUENCE: 12

Xaa Trp Trp Xaa Xaa Trp Ala Xaa Xaa Xaa Arg Xaa Trp Trp Arg
1               5                   10                  15
```

```
<210> SEQ ID NO 13
<211> LENGTH: 19
<212> TYPE: PRT
<213> ORGANISM: Artificial
<220> FEATURE:
<223> OTHER INFORMATION: VEPEP-9-Funct-1
<220> FEATURE:
<221> NAME/KEY: MISC_FEATURE
<222> LOCATION: (1)..(1)
<223> OTHER INFORMATION: residue bound to a Cholesterol, PEGylation,
      stearyl, palmitoyl, small FC or FAB fragments, nanobody,
      nitrilotriacetic acid (2 x NTA), or a tissue targeting peptide
<220> FEATURE:
<221> NAME/KEY: MISC_FEATURE
<222> LOCATION: (12)..(12)
<223> OTHER INFORMATION: X = A or F
<220> FEATURE:
<221> NAME/KEY: MISC_FEATURE
<222> LOCATION: (18)..(18)
<223> OTHER INFORMATION: X = W or F
<220> FEATURE:
<221> NAME/KEY: MISC_FEATURE
<222> LOCATION: (19)..(19)
<223> OTHER INFORMATION: residue bound to CH2-CH2-SH

<400> SEQUENCE: 13

Leu Arg Trp Trp Leu Arg Trp Ala Ser Arg Trp Xaa Ser Arg Trp Ala
1               5                   10                  15

Trp Xaa Arg

<210> SEQ ID NO 14
<211> LENGTH: 19
<212> TYPE: PRT
<213> ORGANISM: Artificial
<220> FEATURE:
<223> OTHER INFORMATION: VEPEP-9-Funct-2
<220> FEATURE:
<221> NAME/KEY: MISC_FEATURE
<222> LOCATION: (1)..(1)
<223> OTHER INFORMATION: acedtylated residue
<220> FEATURE:
<221> NAME/KEY: MISC_FEATURE
<222> LOCATION: (12)..(12)
<223> OTHER INFORMATION: X = A or F
<220> FEATURE:
<221> NAME/KEY: MISC_FEATURE
<222> LOCATION: (18)..(18)
<223> OTHER INFORMATION: X = W or F
<220> FEATURE:
<221> NAME/KEY: MISC_FEATURE
<222> LOCATION: (19)..(19)
<223> OTHER INFORMATION: residue bound to CH2-CH2-S-S-Z, with Z =
      Cholesterol, PEGylation, stearyl, palmitoyl, small FC or FAB
      fragments, nanobody, nitrilotriacetic acid (2 x NTA), or tissues
      targeting peptides

<400> SEQUENCE: 14

Leu Arg Trp Trp Leu Arg Trp Ala Ser Arg Trp Xaa Ser Arg Trp Ala
1               5                   10                  15

Trp Xaa Arg

<210> SEQ ID NO 15
<211> LENGTH: 14
<212> TYPE: PRT
<213> ORGANISM: Artificial
<220> FEATURE:
<223> OTHER INFORMATION: VEPEP-9-Funct-3
<220> FEATURE:
<221> NAME/KEY: MISC_FEATURE
<222> LOCATION: (1)..(1)
<223> OTHER INFORMATION: residue bound to Cholesterol, PEGylation,
```

```
        stearyl, palmitoyl, small FC or FAB fragments, nanobody,
        nitrilotriacetic acid (2 x NTA), or tissues targeting peptides
<220> FEATURE:
<221> NAME/KEY: MISC_FEATURE
<222> LOCATION: (14)..(14)
<223> OTHER INFORMATION: residue bound to CH2-CH2-SH

<400> SEQUENCE: 15

Trp Trp Gly Ser Trp Ala Thr Pro Arg Arg Arg Trp Trp Arg
1               5                   10

<210> SEQ ID NO 16
<211> LENGTH: 14
<212> TYPE: PRT
<213> ORGANISM: Artificial
<220> FEATURE:
<223> OTHER INFORMATION: VEPEP-9-Funct-4
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (14)..(14)
<223> OTHER INFORMATION: residue bound to CH2-CH2-S-S-Z, with
        Z = Cholesterol, PEGylation, stearyl, palmitoyl, small FC or FAB
        fragments, nanobody, nitrilotriacetic acid (2 x NTA), or tissues
        targeting peptides

<400> SEQUENCE: 16

Trp Trp Gly Ser Trp Ala Thr Pro Arg Arg Arg Trp Trp Arg
1               5                   10

<210> SEQ ID NO 17
<211> LENGTH: 21
<212> TYPE: DNA
<213> ORGANISM: Artificial
<220> FEATURE:
<223> OTHER INFORMATION: Cyc-B1 sense

<400> SEQUENCE: 17
ggcgaagauc aacauggcat t                                                 21

<210> SEQ ID NO 18
<211> LENGTH: 21
<212> TYPE: DNA
<213> ORGANISM: Artificial
<220> FEATURE:
<223> OTHER INFORMATION: Cyc-B1 antisense

<400> SEQUENCE: 18
ugccauguug aucuucgcct t                                                 21

<210> SEQ ID NO 19
<211> LENGTH: 21
<212> TYPE: DNA
<213> ORGANISM: Artificial
<220> FEATURE:
<223> OTHER INFORMATION: Cyc-B3 sense

<400> SEQUENCE: 19
ggugaagauc agcauggcat t                                                 21

<210> SEQ ID NO 20
<211> LENGTH: 21
<212> TYPE: DNA
<213> ORGANISM: Artificial
<220> FEATURE:
<223> OTHER INFORMATION: Cyc-B3 antisense
```

```
<400> SEQUENCE: 20
ugccaugucg aucuucacct t                                              21

<210> SEQ ID NO 21
<211> LENGTH: 21
<212> TYPE: DNA
<213> ORGANISM: Artificial
<220> FEATURE:
<223> OTHER INFORMATION: GAPDH sense

<400> SEQUENCE: 21
caucaucccu gccucuacut t                                              21

<210> SEQ ID NO 22
<211> LENGTH: 19
<212> TYPE: DNA
<213> ORGANISM: Artificial
<220> FEATURE:
<223> OTHER INFORMATION: GAPDH antisense

<400> SEQUENCE: 22
aguagaggca gggaugaug                                                 19

<210> SEQ ID NO 23
<211> LENGTH: 10
<212> TYPE: DNA
<213> ORGANISM: Artificial
<220> FEATURE:
<223> OTHER INFORMATION: ODN1

<400> SEQUENCE: 23
agcttagctt                                                           10

<210> SEQ ID NO 24
<211> LENGTH: 17
<212> TYPE: DNA
<213> ORGANISM: Artificial
<220> FEATURE:
<223> OTHER INFORMATION: Cyc-B1a

<400> SEQUENCE: 24
tgccatcggg cttggcy                                                   17

<210> SEQ ID NO 25
<211> LENGTH: 16
<212> TYPE: PRT
<213> ORGANISM: Artificial
<220> FEATURE:
<223> OTHER INFORMATION: VEPEP-3a
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (16)..(16)
<223> OTHER INFORMATION: residue bound to a cysteamide

<400> SEQUENCE: 25

Xaa Lys Trp Phe Glu Arg Trp Phe Arg Glu Trp Pro Arg Lys Arg Arg
1               5                   10                  15
```

```
<210> SEQ ID NO 26
<211> LENGTH: 16
<212> TYPE: PRT
<213> ORGANISM: Artificial
<220> FEATURE:
<223> OTHER INFORMATION: VEPEP-3b
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (16)..(16)
<223> OTHER INFORMATION: residue bound to a cysteamide

<400> SEQUENCE: 26

Xaa Lys Trp Trp Glu Arg Trp Trp Arg Glu Trp Pro Arg Lys Arg Lys
1               5                   10                  15

<210> SEQ ID NO 27
<211> LENGTH: 16
<212> TYPE: PRT
<213> ORGANISM: Artificial
<220> FEATURE:
<223> OTHER INFORMATION: VEPEP-3c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (16)..(16)
<223> OTHER INFORMATION: residue bound to a cysteamide

<400> SEQUENCE: 27

Xaa Arg Trp Trp Glu Lys Trp Trp Thr Arg Trp Pro Arg Lys Arg Lys
1               5                   10                  15

<210> SEQ ID NO 28
<211> LENGTH: 16
<212> TYPE: PRT
<213> ORGANISM: Artificial
<220> FEATURE:
<223> OTHER INFORMATION: VEPEP-3d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (16)..(16)
<223> OTHER INFORMATION: residue bound to a cysteamide

<400> SEQUENCE: 28

Xaa Arg Trp Tyr Glu Lys Trp Tyr Thr Glu Phe Pro Arg Arg Arg Arg
1               5                   10                  15

<210> SEQ ID NO 29
<211> LENGTH: 17
<212> TYPE: PRT
<213> ORGANISM: Artificial
```

```
<220> FEATURE:
<223> OTHER INFORMATION: VEPEP-3e
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (17)..(17)
<223> OTHER INFORMATION: residue bound to a cysteamide

<400> SEQUENCE: 29

Xaa Arg Trp Trp Arg Leu Trp Trp Arg Ser Trp Phe Arg Leu Trp Arg
1               5                   10                  15

Arg

<210> SEQ ID NO 30
<211> LENGTH: 17
<212> TYPE: PRT
<213> ORGANISM: Artificial
<220> FEATURE:
<223> OTHER INFORMATION: VEPEP-3f
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (17)..(17)
<223> OTHER INFORMATION: residue bound to a cysteamide

<400> SEQUENCE: 30

Xaa Leu Trp Trp Arg Arg Trp Trp Ser Arg Trp Trp Pro Arg Trp Arg
1               5                   10                  15

Arg

<210> SEQ ID NO 31
<211> LENGTH: 17
<212> TYPE: PRT
<213> ORGANISM: Artificial
<220> FEATURE:
<223> OTHER INFORMATION: VEPEP-3g
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (17)..(17)
<223> OTHER INFORMATION: residue bound to a cysteamide

<400> SEQUENCE: 31

Xaa Leu Trp Trp Ser Arg Trp Trp Arg Ser Trp Phe Arg Leu Trp Phe
1               5                   10                  15

Arg

<210> SEQ ID NO 32
<211> LENGTH: 17
```

```
<212> TYPE: PRT
<213> ORGANISM: Artificial
<220> FEATURE:
<223> OTHER INFORMATION: VEPEP-3h
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (17)..(17)
<223> OTHER INFORMATION: residue bound to a cysteamide

<400> SEQUENCE: 32

Xaa Lys Phe Trp Ser Arg Phe Trp Arg Ser Trp Phe Arg Leu Trp Arg
1               5                   10                  15

Arg

<210> SEQ ID NO 33
<211> LENGTH: 19
<212> TYPE: PRT
<213> ORGANISM: Artificial
<220> FEATURE:
<223> OTHER INFORMATION: VEPEP-6a
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (19)..(19)
<223> OTHER INFORMATION: residue bound to a cysteamide

<400> SEQUENCE: 33

Xaa Leu Phe Arg Ala Leu Trp Arg Leu Leu Arg Ser Leu Trp Arg Leu
1               5                   10                  15

Leu Trp Lys

<210> SEQ ID NO 34
<211> LENGTH: 20
<212> TYPE: PRT
<213> ORGANISM: Artificial
<220> FEATURE:
<223> OTHER INFORMATION: VEPEP-6b
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue bound to a cysteamide

<400> SEQUENCE: 34

Xaa Leu Trp Arg Ala Leu Trp Arg Leu Trp Arg Ser Leu Trp Arg Leu
1               5                   10                  15

Leu Trp Lys Ala
            20
```

```
<210> SEQ ID NO 35
<211> LENGTH: 20
<212> TYPE: PRT
<213> ORGANISM: Artificial
<220> FEATURE:
<223> OTHER INFORMATION: VEPEP-6c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue bound to a cysteamide

<400> SEQUENCE: 35

Xaa Leu Trp Arg Ala Leu Trp Arg Leu Leu Arg Ser Leu Trp Arg Leu
1               5                   10                  15

Trp Arg Lys Ala
            20

<210> SEQ ID NO 36
<211> LENGTH: 20
<212> TYPE: PRT
<213> ORGANISM: Artificial
<220> FEATURE:
<223> OTHER INFORMATION: VEPEP-6d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue bound to a cysteamide

<400> SEQUENCE: 36

Xaa Leu Trp Arg Ala Leu Trp Arg Leu Trp Arg Ser Leu Trp Arg Leu
1               5                   10                  15

Trp Arg Lys Ala
            20

<210> SEQ ID NO 37
<211> LENGTH: 20
<212> TYPE: PRT
<213> ORGANISM: Artificial
<220> FEATURE:
<223> OTHER INFORMATION: VEPEP-6e
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue bound to a cysteamide

<400> SEQUENCE: 37

Xaa Leu Trp Arg Ala Leu Trp Arg Leu Leu Arg Ala Leu Trp Arg Leu
```

```
1               5                   10                  15

Leu Trp Lys Ala
            20

<210> SEQ ID NO 38
<211> LENGTH: 20
<212> TYPE: PRT
<213> ORGANISM: Artificial
<220> FEATURE:
<223> OTHER INFORMATION: VEPEP-6f
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (20)..(20)
<223> OTHER INFORMATION: residue bound to a cysteamide

<400> SEQUENCE: 38

Xaa Leu Trp Arg Ala Leu Trp Arg Leu Leu Arg Asn Leu Trp Arg Leu
1               5                   10                  15

Leu Trp Lys Ala
            20

<210> SEQ ID NO 39
<211> LENGTH: 17
<212> TYPE: PRT
<213> ORGANISM: Artificial
<220> FEATURE:
<223> OTHER INFORMATION: VEPEP-3bstapl
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (3)..(3)
<223> OTHER INFORMATION: X = R, which is linked to the R residue at
      position 10 by a hydrocarbon linkage
<220> FEATURE:
<221> NAME/KEY: MISC_FEATURE
<222> LOCATION: (10)..(10)
<223> OTHER INFORMATION: X = R, which is linked to the R residue at
      position 3 by a hydrocarbon linkage
<220> FEATURE:
<221> NAME/KEY: MISC_FEATURE
<222> LOCATION: (17)..(17)
<223> OTHER INFORMATION: residue bound to a cysteamide

<400> SEQUENCE: 39

Xaa Lys Xaa Trp Trp Glu Arg Trp Trp Xaa Ser Trp Pro Arg Lys Arg
1               5                   10                  15

Lys

<210> SEQ ID NO 40
<211> LENGTH: 17
<212> TYPE: PRT
<213> ORGANISM: Artificial
<220> FEATURE:
<223> OTHER INFORMATION: VEPEP-3estapl
<220> FEATURE:
<221> NAME/KEY: MISC_FEATURE
```

```
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (5)..(5)
<223> OTHER INFORMATION: X = R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the R residue at
      position 5 by a hydrocarbon linkage
<220> FEATURE:
<221> NAME/KEY: MISC_FEATURE
<222> LOCATION: (17)..(17)
<223> OTHER INFORMATION: residue bound to a cysteamide

<400> SEQUENCE: 40

Xaa Arg Trp Trp Xaa Leu Trp Trp Arg Ser Trp Xaa Arg Leu Trp Arg
1               5                   10                  15

Arg

<210> SEQ ID NO 41
<211> LENGTH: 19
<212> TYPE: PRT
<213> ORGANISM: Artificial
<220> FEATURE:
<223> OTHER INFORMATION: ST-VEPEP-6a
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X = R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the R residue at
      position 8 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 41

Xaa Leu Phe Arg Ala Leu Trp Xaa Leu Leu Arg Xaa Leu Trp Arg Leu
1               5                   10                  15

Leu Trp Lys

<210> SEQ ID NO 42
<211> LENGTH: 19
<212> TYPE: PRT
<213> ORGANISM: Artificial
<220> FEATURE:
<223> OTHER INFORMATION: ST-VEPEP-6aa
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
```

-continued

```
<223> OTHER INFORMATION: X = beta-A or S
<220> FEATURE:
<221> NAME/KEY: MISC_FEATURE
<222> LOCATION: (8)..(8)
<223> OTHER INFORMATION: X = R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the R residue at
      position 8 by a hydrocarbon linkage
<220> FEATURE:
<221> NAME/KEY: MISC_FEATURE
<222> LOCATION: (19)..(19)
<223> OTHER INFORMATION: residue bound to a  cysteamide

<400> SEQUENCE: 42

Xaa Leu Phe Leu Ala Arg Trp Xaa Leu Leu Arg Xaa Leu Trp Arg Leu
1               5                   10                  15

Leu Trp Lys

<210> SEQ ID NO 43
<211> LENGTH: 19
<212> TYPE: PRT
<213> ORGANISM: Artificial
<220> FEATURE:
<223> OTHER INFORMATION: ST-VEPEP-6ab
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X = S, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X = S, which is linked to the S residue at
      position 8 by a hydrocarbon linkage
<220> FEATURE:
<221> NAME/KEY: MISC_FEATURE
<222> LOCATION: (19)..(19)
<223> OTHER INFORMATION: residue bound to a  cysteamide

<400> SEQUENCE: 43

Xaa Leu Phe Arg Ala Leu Trp Xaa Leu Leu Arg Xaa Leu Trp Arg Leu
1               5                   10                  15

Leu Trp Lys

<210> SEQ ID NO 44
<211> LENGTH: 19
<212> TYPE: PRT
<213> ORGANISM: Artificial
<220> FEATURE:
<223> OTHER INFORMATION: ST-VEPEP-6ad
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (8)..(8)
<223> OTHER INFORMATION: X =  S, which is linked to the S residue at
```

```
      position 12 by a hydrocarbon linkage
<220> FEATURE:
<221> NAME/KEY: MISC_FEATURE
<222> LOCATION: (12)..(12)
<223> OTHER INFORMATION: X =  S, which is linked to the S residue at
      position 8 by a hydrocarbon linkage
<220> FEATURE:
<221> NAME/KEY: MISC_FEATURE
<222> LOCATION: (19)..(19)
<223> OTHER INFORMATION: residue bound to a  cysteamide

<400> SEQUENCE: 44

Xaa Leu Phe Leu Ala Arg Trp Xaa Leu Leu Arg Xaa Leu Trp Arg Leu
1               5                   10                  15

Leu Trp Lys

<210> SEQ ID NO 45
<211> LENGTH: 19
<212> TYPE: PRT
<213> ORGANISM: Artificial
<220> FEATURE:
<223> OTHER INFORMATION: ST-VEPEP-6b
<220> FEATURE:
<221> NAME/KEY: MISC_FEATURE
<222> LOCATION: (1)..(1)
<223> OTHER INFORMATION: X = an acetyl
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X =  R, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X =  S, which is linked to the R residue at
      position 11 by a hydrocarbon linkage
<220> FEATURE:
<221> NAME/KEY: MISC_FEATURE
<222> LOCATION: (19)..(19)
<223> OTHER INFORMATION: residue bound to a  cysteamide

<400> SEQUENCE: 45

Xaa Leu Phe Arg Ala Leu Trp Arg Leu Leu Xaa Ser Leu Trp Xaa Leu
1               5                   10                  15

Leu Trp Lys

<210> SEQ ID NO 46
<211> LENGTH: 19
<212> TYPE: PRT
<213> ORGANISM: Artificial
<220> FEATURE:
<223> OTHER INFORMATION: ST-VEPEP-6ba
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X =  R, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X =  S, which is linked to the R residue at
```

-continued

```
      position 11 by a hydrocarbon linkage
<220> FEATURE:
<221> NAME/KEY: MISC_FEATURE
<222> LOCATION: (19)..(19)
<223> OTHER INFORMATION: residue bound to a  cysteamide

<400> SEQUENCE: 46

Xaa Leu Phe Leu Ala Arg Trp Arg Leu Leu Xaa Ser Leu Trp Xaa Leu
1               5                   10                  15

Leu Trp Lys

<210> SEQ ID NO 47
<211> LENGTH: 19
<212> TYPE: PRT
<213> ORGANISM: Artificial
<220> FEATURE:
<223> OTHER INFORMATION: ST-VEPEP-6bb
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X =  S, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X =  S, which is linked to the S residue at
      position 11 by a hydrocarbon linkage
<220> FEATURE:
<221> NAME/KEY: MISC_FEATURE
<222> LOCATION: (19)..(19)
<223> OTHER INFORMATION: residue bound to a  cysteamide

<400> SEQUENCE: 47

Xaa Leu Phe Arg Ala Leu Trp Arg Leu Leu Xaa Ser Leu Trp Xaa Leu
1               5                   10                  15

Leu Trp Lys

<210> SEQ ID NO 48
<211> LENGTH: 19
<212> TYPE: PRT
<213> ORGANISM: Artificial
<220> FEATURE:
<223> OTHER INFORMATION: ST-VEPEP-6bd
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (11)..(11)
<223> OTHER INFORMATION: X =  S, which is linked to the S residue at
      position 15 by a hydrocarbon linkage
<220> FEATURE:
<221> NAME/KEY: MISC_FEATURE
<222> LOCATION: (15)..(15)
<223> OTHER INFORMATION: X =  S, which is linked to the S residue at
      position 11 by a hydrocarbon linkage
<220> FEATURE:
<221> NAME/KEY: MISC_FEATURE
<222> LOCATION: (19)..(19)
<223> OTHER INFORMATION: residue bound to a  cysteamide
```

```
<400> SEQUENCE: 48

Xaa Leu Phe Leu Ala Arg Trp Arg Leu Leu Xaa Ser Leu Trp Xaa Leu
1               5                   10                  15

Leu Trp Lys

<210> SEQ ID NO 49
<211> LENGTH: 19
<212> TYPE: PRT
<213> ORGANISM: Artificial
<220> FEATURE:
<223> OTHER INFORMATION: ST-VEPEP-6c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: X = beta-A or S
<220> FEATURE:
<221> NAME/KEY: MISC_FEATURE
<222> LOCATION: (5)..(5)
<223> OTHER INFORMATION: X =  R, which is linked to the S residue at
      position 12 by a hydrocarbon linkage
<220> FEATURE:
<221> NAME/KEY: MISC_FEATURE
<222> LOCATION: (12)..(12)
<223> OTHER INFORMATION: X =  S, which is linked to the R residue at
      position 5 by a hydrocarbon linkage
<220> FEATURE:
<221> NAME/KEY: MISC_FEATURE
<222> LOCATION: (19)..(19)
<223> OTHER INFORMATION: residue bound to a  cysteamide

<400> SEQUENCE: 49

Xaa Leu Phe Ala Xaa Leu Trp Arg Leu Leu Arg Xaa Leu Trp Arg Leu
1               5                   10                  15

Leu Trp Lys

<210> SEQ ID NO 50
<211> LENGTH: 12
<212> TYPE: PRT
<213> ORGANISM: Artificial
<220> FEATURE:
<223> OTHER INFORMATION: C4

<400> SEQUENCE: 50

Lys Lys Gln Val Arg Met Ala His Leu Val Leu Thr
1               5                   10

<210> SEQ ID NO 51
<211> LENGTH: 4
<212> TYPE: PRT
<213> ORGANISM: Artificial
<220> FEATURE:
<223> OTHER INFORMATION: polypeptide

<400> SEQUENCE: 51

Gly Trp Ser Cys
1

<210> SEQ ID NO 52
<211> LENGTH: 5
<212> TYPE: PRT
<213> ORGANISM: Artificial
<220> FEATURE:
<223> OTHER INFORMATION: Polypeptide
```

```
<400> SEQUENCE: 52

Gly Trp Ala Ser Cys
1               5

<210> SEQ ID NO 53
<211> LENGTH: 12
<212> TYPE: PRT
<213> ORGANISM: Artificial
<220> FEATURE:
<223> OTHER INFORMATION: C2S

<400> SEQUENCE: 53

Val Thr Leu Met Glu Ala Lys Lys Gln Val Leu Thr
1               5                   10

<210> SEQ ID NO 54
<211> LENGTH: 12
<212> TYPE: PRT
<213> ORGANISM: Artificial
<220> FEATURE:
<223> OTHER INFORMATION: C2

<400> SEQUENCE: 54

Lys Lys Gln Val Leu Ala Met Glu His Leu Val Thr
1               5                   10
```